United States Patent [19]

Shimada et al.

[11] Patent Number: 5,962,326
[45] Date of Patent: *Oct. 5, 1999

[54] HYPERTHERMOSTABLE β-GALACTOSIDASE GENE, ENZYME ENCODED THEREBY, AND PROCESS FOR PRODUCTION

[76] Inventors: Atsushi Shimada, 5-14-14-1309, Nango, Otsu-shi, Shiga-ken; Miki Odate, 2-12-1-502, Nishishibukawa, Kusatu-shi, Shiga-ken; Nobuto Koyama, 96, Kubo, Ogura-cho, Uji-shi, Kyoto-fu; Kimikazu Hashino, 27-3, Akeno-cho, Takatsuki-shi, Osaka-fu; Kiyozo Asada, 3-20-9, Kibogaoka, Konan-cho, Koga-gun, Shiga-ken; Ikunoshin Kato, 1-1-150, Nanryo-cho, Uji-shi, Kyoto-fu, all of Japan

[*] Notice: This patent is subject to a terminal disclaimer.

[21] Appl. No.: 08/993,581

[22] Filed: Dec. 18, 1997

Related U.S. Application Data

[60] Division of application No. 08/489,733, Jun. 14, 1995, Pat. No. 5,744,345, which is a continuation-in-part of application No. 08/175,533, Dec. 30, 1993, abandoned, which is a continuation-in-part of application No. 08/128,079, Sep. 29, 1993, abandoned.

[30] Foreign Application Priority Data

| Oct. 5, 1992 | [JP] | Japan | 4-288156 |
| Jan. 8, 1993 | [JP] | Japan | 5-16846 |
| Dec. 6, 1993 | [JP] | Japan | 5-339188 |
| Jun. 14, 1994 | [JP] | Japan | 6-154356 |

[51] Int. Cl.$^6$ .......................... C12N 15/56; C12N 15/10; C12N 15/63
[52] U.S. Cl. .............................. 435/440; 435/6; 435/207; 435/471; 435/476; 536/23.1; 536/23.2
[58] Field of Search ................... 536/23.2, 23.1; 435/6, 207, 440, 471, 476

[56] References Cited

U.S. PATENT DOCUMENTS

| 3,816,259 | 6/1974 | Collinge et al. | 195/62 |
| 3,919,049 | 11/1975 | Kiuchi et al. | 195/66 |
| 4,229,539 | 10/1980 | Miwa et al. | 435/207 |
| 5,082,785 | 1/1992 | Manning et al. | 435/252.32 |
| 5,242,817 | 9/1993 | Kelly et al. | 435/220 |
| 5,283,189 | 2/1994 | Takase et al. | 435/207 |

FOREIGN PATENT DOCUMENTS

| 279778 | 8/1988 | European Pat. Off. . |
| 0 592 158 | 7/1994 | European Pat. Off. . |
| 0 606 008 | 7/1994 | European Pat. Off. . |
| 56-154991 | 11/1981 | Japan . |

OTHER PUBLICATIONS

Fems Microbiology Letters, vol. 109, 1993 pp. 131–138, Josef Gabelsberger et al. "Cloning and characterization of beta–galactoside and beta–glucoside hydrolysing enzymes of thermotoga maritima", p. 131, right column, paragraph 2—p. 132, left column, paragraph 2, p. 133, left column, paragraph 2—p. 134, right column, paragraph 1.

Journal of Applied Biochemistry, vol. 2, No. 5, 1980, pp. 390–397, Vincenzo Buonocore et al., "A constitutive beta–galactosidase from the extreme thermoacidophile archaebacterium caldariella acidophila: Properties of the enzyme in the free state and immobilized whole cells", abstract, p. 390, paragraph 2—p. 391, paragraph 1, p. 394, paragraph 1, p. 395, paragraph 4—p. 396, paragraph 1.

International Journal of Biochemistry, vol. 5, 1974, pp. 629–632, Robert P. Erickson "Stability of *Escherichia coli* beta–galatosidase in sodium dodecyl sulfate" abstract, p. 629, left column, paragraph 1.

Y. Koyama et al., "Cloning of Alpha and β–Galactosidase Genes From an Extreme Thermophile, Thermus Strain T2, and Their Expression in Thermus Thermophilus HB27", Appl. Environ. Microbiol. 56(7); pp. 2251–2254.

M.V. Cubellis et al., "Isolation and Sequencing of a New β–Galactosidase–Encoding Archaebacterial Gene", Gene, 94: pp. 89–94.

Critical Reviews in Food Technology, Jan. 1975, pp. 330–355, CRC Press.

Kengen et al., "Purification and characterization of an extremely thermostable β–glucosidase from the hyperthermophilic archaeon *Pyrococcus furiosus*", Eur. J. Biochem. 213, pp. 305–312 (1993).

Costantino et al., "Purification and characterization of an α–glucosidase from a hyperthermophilic archaebacterium, *Pyrococcus furiosus*, exhibiting a temperature optimum of 105 to 115°C", Journal of Bacteriology, 172 (7), pp. 3654–3660, Jul. 1990.

Wozney et al., "Using purified protein to clone its gene", Method Enzymol, 182, pp. 738–749, 1990.

Cubellis et al., "Isolation and sequencing of a new β–galactosidase–encoding archaebacterial gene", Gene 94, pp. 89–94, 1990.

Moracci et al., "Expression of the thermostable β–galactosidase gene from the arcbaebacterium *Sulfolobus solfataricus* in *Saccharomyces cerevisiae* and characterization of a new inducible promoter for heterologous expression", Journal of Bacteriology, vol. 174, No. 3, pp. 873–882, Feb. 1992.

Pisani et al., "Thermostable β–galactosidase from the archaebacterium *Solfolobus solfataricus* purification and properties", Eur. J. Biochem. 187, pp. 321–328, 1990.

M.V. Cubellis et al., "Isolation and Sequencing of a New β–Galactosidase–Encoding Archaebacterial Gene", Gene 94: 89–94, 1990.

*Primary Examiner*—Rebecca E. Prouty
*Attorney, Agent, or Firm*—Wenderoth, Lind & Ponack, L.L.P.

[57] ABSTRACT

An isolated SDS-resistant hyperthermostable β-galactosidase gene derived from *Pyrococcus furiosus*. Examples thereof include genes respectively shown in SEQ ID NO: 1 and SEQ ID NO: 2 and genes each hybridizable with the above gene shown in SEQ ID NO: 1. A method of cloning the hyperthermostable β-galactosidase gene in which each of the above genes or pacts thereof is used as a probe or primer. A process for producing a hyperthermostable β-galactosidase by culturing a transformant into which a plasmid containing each of the above gene has been introduced.

7 Claims, 14 Drawing Sheets

FIG. 21

```
           10             20  Box-1  30              40           50   Box-2  60
  1 M--FPEKFLW GVAQSGFQFE MGDKLRRNID TNTDWWHWVR DKTNIEKGLV SGDLPEEGIN  60
  1 M-KFPKNFMF GYSWSGFQFE MGLPGSEV-- -ESDWWVWVH DKENIASGLV SGDLPENGPA  60
  1 MLSFPKGFKF GWSQSGFQSE MGTPGSEDP- -NSDWHVWVH DRENIVSQVV SGDLPENGPG  60
  1 MYSFPNSFRF GWSQAGFQSE MGTPGSEDP- -NTDWYKWVH DPENMAAGLV SGDLPENGPG  60
           70             80             90  Box-3 100            110            120
 61 NYELYEKDHE IARKLGLNAY RIGIEWSRIF PWETTFIDVD YSYNESYNLI EDVKITKDTL 120
 61 YWHLYKQDHD IAEKLGMDCI RGGIEWARIF PKPTFDVKVD -VEKDEEGNI ISVDVPESTI 120
 61 YWGNYKRFHD EAEKIGLNAV RINVEWSRIF PRPLPKPEMQ TGTDKENSPV ISVDLNESKL 120
 61 YWGNYKTFHD NAQKMGLKIA RLNVEWSRIF PNPLPRPQNF ---DESKQDV TEVEINENEL 120
          130            140            150            160   Box-4 170            180
121 EELDEIANKR EVAYYRSVIN SLRSKGFKVI VNLNHFT--L PYWLHDPIEA RERALTNKRN 180
121 KELEKIANME ALEHYRKIYS DWKERGKTFI --LNLYHWPL PLWIHDPIAV RKLGPDRAPA 180
121 REMDNYANHE ALSHYRHILE DLRNRGFHIV --LNMYHWTL PIWLHDPIRV RRGDFT-GPT 180
121 KRLDEYANKD ALNHYREIFK DLKSRGLYFI --LNMYHWPL PLWLHDPIRV RRGDFT-GPS 180
          190            200            210     Box-5 220            230            240
181 GWVNPRTVIE FAKYAAYIAY KFGDIVDMWS TFNEPMVVE  LGYLAPYSGF PPGVLNPEAA 240
181 GWLDEKTVVE FVKFAAFVAY HLDDLVDMWS TMNEPNVVYN QGYINLRSGF PPGYLSFEAA 240
181 GWLNSRTVYE FARFSAYVAW KLDDLASEYA TMNEPNVVWG AGYAFPRAGF PPNYLSFRLS 240
181 GWLSTRTVYE FARFSAYIAW KFDDLVDEYS TMNEPNVVGG LGYVGVKSGF PPGYLSFELS 240
          250   Box-6  260            270            280            290            300
241 KLAILHMINA HALAYRQIKK FDTEKADKDS KEPAEVGIIY NNIGVAYPKD PNDSKDVKAA 300
241 EKAKFNLIQA HIGAYDAIKE Y--------- --------- -SEKSVGVIY AFA------- 300
241 EIAKWNIIQA HARAYDAIKS V--------- --------- -SKKSVGIIY ANT------- 300
241 RRHMYNIIQA HARAYDGIKS V--------- --------- -SKKPVGIIY ANS------S 300
```

FIG. 22

```
        310        320        330        340  Box-7 350        360
301 ENDNFFHSGL FFEAIHKGKL NIEFDGETFI DAPYLKGNDW IGVNYYTREV VTYQEPMFPS 360
301 -----WHDPL AEEYKDEVEE IRKKDYEFVT ILHSKGKLDW IGVNYYSRLV YG-------- 360
301 EAVEIAERLN RWSFFDSIIK GEITSEGQNV REDLRNRLDW IGVNYYTRTV VTK------- 360
301 AVEMAENDNR WWFFDAIIRG EITRGNEKIV RDDLKGRLDW IGVNYYTRTV VKR------- 360

370        380    Box-8 400        410        420
361 IPLITFKGVQ GYGYACRPGT LSKDDRPVSD IGWELYPEGM YD-SIVEAHK YGVPVYVTEN 420
361 AKDGHLVPLP GYGFMSERGG FAKSGRPASD FGWEMYPEGL ENLLKYLNNA YELPMIITEN 420
361 -AESGYLTLP GYGDRCERNS LSLANLPTSD FGWEFFPEGL YDVLLKYWNR YGLPLYVMEN 420
361 -TEKGYVSLG GYGHGCERNS VSLAGLPTSD FGWEFFPEGL YDVLTKYWNR YHLYMYVTEN 420

430  Box-9 440        450        460 Box-10 470        480
421 GIADSKDILR PYYIASHIKM IEKAFEDGYE VKGYFHWALT DNFEWALGFR MRFGLYEVNL 480
421 GMADAADRYR PHYLVSHLKA VYNAMKEGAD VRGYLHWSLT DNYEWAQGFR MRFGLVYVDF 480
421 GIADDADYQR PYYLVSHIYQ VHRALNEGVD VRGYLHWSLA DNYEWSSGFS MRFGLLKVDY 480
421 GIADDADYQR PYYLVSHVYQ VHRAINSGAD VRGYLHWSLA DNYEWASGFS MRFGLLKVDY 480

490        500        510        520        530        540
481 ITKERIPREK SVSIFREIVA NNGVTKKIEE ELLRG*.... .......... .......... 540
481 ETKKRYLRP- SALVFREIAT ----QKEIPE ELAHLADLKF VTKKVAISFF LCFLTHIFGK 540
481 LTKRLYWRP- SALVYREITR SNG----IPE ELEHLNRVPP IKPLRH.... .......... 540
481 NTKRLYWRP- SALVYREIAT -NGAITDEIE HLNSVPPVKP LRH....... .......... 540

550        560        570        580        590        600
541 .......... .......... .......... .......... .......... .......... 600
541 IRS*...... .......... .......... .......... .......... .......... 600
541 .......... .......... .......... .......... .......... .......... 600
541 .......... .......... .......... .......... .......... .......... 600
```

HYPERTHERMOSTABLE β-GALACTOSIDASE GENE, ENZYME ENCODED THEREBY, AND PROCESS FOR PRODUCTION

This application is a Rule 53(b) divisional application of Ser. No. 08/489.733 filed Jun. 14, 1995 now U.S. Pat. No. 5,744,345 which is a continuation-in-part of now abandoned application Ser. No. 08/175,533 filed Dec. 30, 1993, which is a continuation-in-part of now abandoned application Ser. No. 08/128,079 filed Sep. 29, 1993.

BACKGROUND OF THE INVENTION

1. Field of the Invention

This invention relates to a β-galactosidase, including an SDS-resistant β-galactosidase, which has a hyperthermostability and is useful in the food industry and a process for producing the same.

The invention also relates to a gene coding for the hyperthermostable β-galactosidase and a genetic engineering process for producing the enzyme which is useful in the fields of, for example, food industry and saccharide engineering.

2. Description of Related Art

β-galactosidase, which is an enzyme capable of decomposing β-galactoside, has been discovered in animals, plants and microorganisms. It is known that this enzyme occurs particularly in bacteria such as *Escherichia coli, Streptococcus lactis, Bacillus subtillis, Streptococcus thermophilus* and *Sulfolobus solfataricus*. Such a β-galactosidase is applied to the production of low-lactose milk by taking advantage of its ability to hydrolyze lactose into galactose and glucose. It is also applied to the production of galactose or glucose from lactose contained in milk serum which is formed in a large amount in the processor producing cheese.

To apply a β-galactosidase to food processing, therefore, it has been demanded to develop an enzyme that can withstand its use at a high temperature from the viewpoint of preventing contamination with microorganisms during processing and from another viewpoint of elevating the solubility of lactose which serves as a substrate.

Further, in recent years, various sugar compound productions are conducted with the use of a β-galactosidase glycosyltransfer reaction [Japanese Patent Laid-Open No. 25275/1994 and Japanese Patent Laid-Open 14774/1994]. Thus, the development of highly thermostable enzymes is desired.

For example, a β-galactosidase originating in *Sulfolobus solfataricus* [see *European Journal of Biochemistry*, 187, 321–328 (1990)] is a thermophilic enzyme having an activity at a temperature of 90° C. However, its activity falls to about 50% after treating at 85° C. for 180 minutes.

It is described in, for example, *European Journal of Biochemistry*, 213, 305–312 (1993), that β-galactosidase derived from the hyperthermophilic bacterium *Pyrococcus furiosus* exhibits its activity at high temperatures, thereby ensuring a high thermostability.

The inventors have discovered a hyperthermostable β-galactosidase having a residual activity ratio of about 80% even after treatment at 90° C. for 120 minutes and succeeded in isolating three types of β-galactosidases [European Patent Laid-Open No. 0592158A2]. These three types of β-galactosidases are all hyperthemostable, and one of them is a β-galactosidase having an extremely high stability and exhibits its activity even in the presence of 1% sodium dodecyl sulfate (SDS).

SUMMARY OF THE INVENTION

As mentioned above, a thermophilic and thermostable enzyme is demanded in food processing and sugar compound production conducted at high temperatures. Further, if an enzyme holds its activity even in the presence of SDS which is known as a powerful surfactant, its application range can be widened.

In order to solve these problems, the present invention provides a β-galactosidase having an improved thermophilicity and an excellent thermostability.

The present invention also provides a gene coding for β-galactosidase having an improved thermophilicity and an excellent thermostability and provides a process for producing the hyperthermostable β-galactosidase with the use of the gene.

A further object of the present invention is to isolate a gene encoding a β-galactosidase having an improved thermophilicity, an excellent thermostability and resistance to surfactants, and to an industrial process for producing a hyperthermostable β-galactosidase with the use of the above gene.

To sum up the present invention, the first invention relates to a hyperthermostable β-galactosidase characterized by having a residual activity of about 80% or above after having been treated at 90° C. for 120 minutes.

The second invention relates to a process for producing a hyperthermostable β-galactosidase characterized by cultivating a bacterium of the genus Pyrococcus and recovering the β-galactosidase from the culture.

The third invention relates to an isolated DNA encoding a hyperthermophilic β-galactosidase which has the amino acid sequence shown in SEQ. ID NO. 1 of the Sequence Listing.

The fourth invention relates to an isolated DNA encoding a hyperthermophilic β-galactosidase of the third invention, which has the DNA sequence shown in SEQ. ID NO. 2 of the Sequence Listing.

The fifth invention relates to an isolated DNA encoding a hyperthermophilic β-galactosidase and having a DNA sequence which hybridizes with a DNA sequence of the third invention or fourth invention under stringent conditions.

The sixth invention relates to a process for producing a hyperthermostable β-galactosidase which comprises:
(a) constructing a plasmid in which an isolated DNA encoding a hyperthermophilic β-galactosidase as claimed in any one of the third to fifth inventions is inserted;
(b) transforming an appropriate host organism with said plasmid; and
(c) cultivating the transformed host organism and recovering the hyperthermophilic β-galactosidase from the culture.

The seventh invention relates to an isolated SDS-resistant hyperthermophilic β-galactosidase gene derived from *Pyrococcus furiosus*.

The eighth invention relates to the gene according to the seventh invention, which encodes a portion having an amino acid sequence shown in SEQ ID NO. 3 or a part thereof and having a hyperthermophilic β-galactosidase enzyme activity.

The ninth invention relates to the gene according to the seventh invention, which has a nucleotide sequence shown in SEQ ID NO. 4.

The tenth invention relates to an SDS-resistant hyperthermophilic β-galactosidase gene, which is hybridizable with the gene according to the eighth invention.

The eleventh invention relates to a method of cloning a hyperthermophilic β-galactosidase gene, which comprises using a gene according to any of the eighth to tenth inventions or a part thereof as a probe or a primer.

The twelfth invention relates to a process for producing a hyperthermophilic β-galactosidase, which comprises culturing a transformant, into which a recombinant plasmid containing the hyperthermophilic β-galactosidase gene according to the seventh invention has been introduced, and harvesting a hyperthermostable β-galactosidase from the culture.

BRIEF DESCRIPTION OF THE DRAWINGS

FIG. 21 shows part (first half) of a view comparing amino acid sequences of various β-galactosidases.

FIG. 22 shows part (latter half) of a view comparing amino acid sequences of various β-galactosidases.

DETAILED DESCRIPTION OF THE PREFERRED EMBODIMENTS

Figure 1:
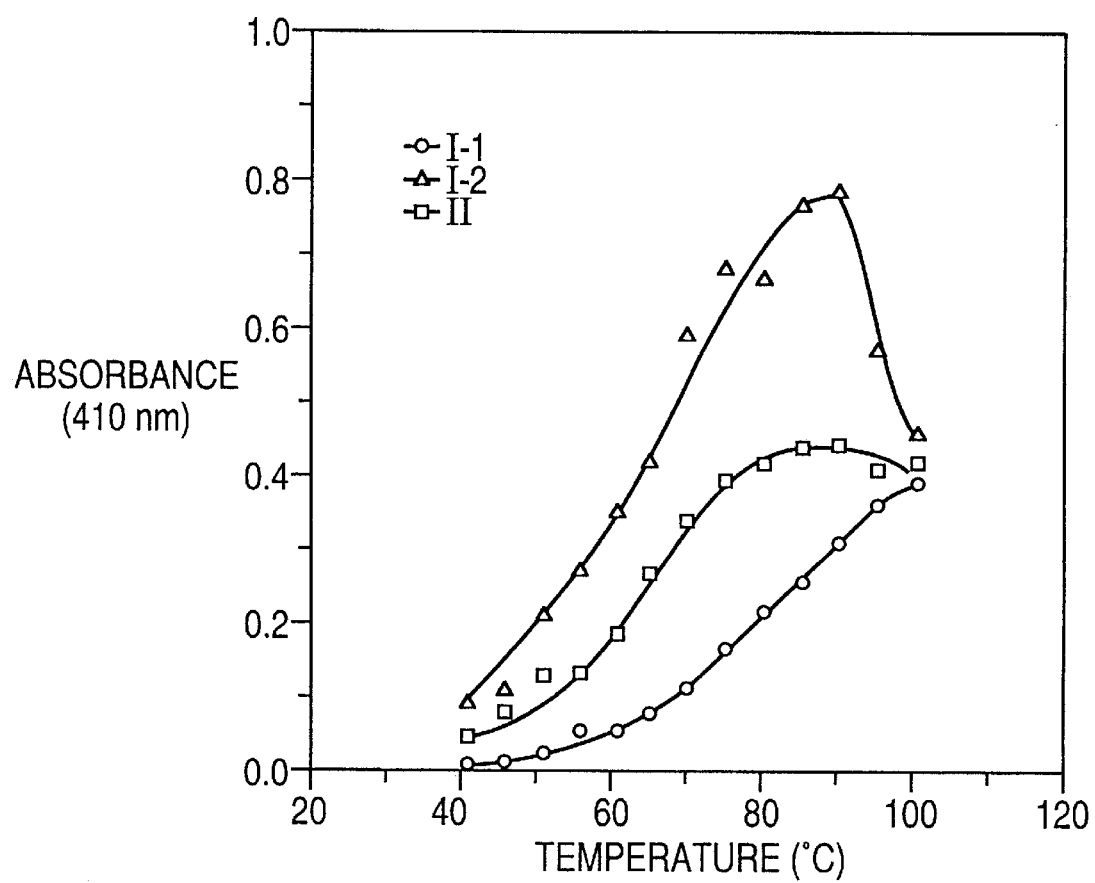
FIG. 1 is a graph showing the relationships between the activities of the enzymes of the present invention with the use of o-nitrophenyl-β-D-galactopyranoside as a substrate and temperature, wherein the ordinate refers to the absorbance at 410 nm of the enzymatic reaction product while the abscissa refers to temperature.

The microorganism to be used in the present invention is not particularly restricted, so long as it produces a hyperthermostable β-galactosidase. For example, strains belonging to the genus Pyrococcus exemplified by *Pyrococcus furiosus* DSM 3638 and *Pyrococcus woesei* DSM 3773 are usable therefor. Such a strain is cultivated in an appropriate growth medium and then the hyperthermophilic β-galactosidase according to the present invention can be obtained from the cells and the culture.

Now, the present invention will be described by referring to the use of a strain of the genus Pyrococcus as an example.

To cultivate a bacterium of the genus Pyrococcus, a method usually employed for cultivating a hyperthermostable bacterium may be used. Any nutrient which can be utilized by the employed strain may be added to the medium. For example, starch is usable as a carbon source and trypton and peptone are usable as a nitrogen source. As other nutrients, yeast extract and the like can be used. The medium may contain metal salts such as magnesium salts, sodium salts or iron salts as a trace element. It is advantageous to use artificial seawater for the preparation of the medium, as done in the present invention. The medium is preferably a transparent one free from a solid sulfur element, since such a medium makes it easy to monitor the growth of the cells by measuring the optical density of the culture. The cultivation can be effected either stationarily or under stirring. Alternatively, an aeration culture [see Japanese Patent Publication No. 503757/1992] or a dialysis culture [see *Appl. Env. Microbiol.*, 55, 2086–2088 (1992)] may be carried out. In general, the cultivation temperature is preferably around 95° C. Usually, a considerably large amount of the β-galactosidase is accumulated in the culture within about 16 hours. It is a matter of course that the cultivation conditions should be determined in such a manner as to achieve the maximum yield of the β-galactosidase depending on the selected strain and the composition of the medium.

A β-galactosidase of the present invention can be recovered by, for example, collecting the cells from the culture broth by centrifuging or filtering and then disrupting the cells. The cell disruption can be effected by, for example, ultrasonic disruption, bead disruption of lytic enzyme treatment. By using these techniques, the β-galactosidase according to the present invention can be extracted from the cells. The enzyme may be extracted by a method capable of giving the highest extraction effect depending on the selected bacterium and thus a crude enzyme solution is obtained. From the crude enzyme solution thus obtained, the β-galactosidase can be isolated by combining technique commonly employed for purifying enzymes, for example, salting out with ammonium sulfate, ion exchange chromatography, hydrophobic chromatography and gel filtration.

For example, a crude enzyme solution prepared from cultivated cells of *Pyrococcus furiosus* DSM 3638 is chromatographed with a DEAE Toyopearl M650 ion exchanger (mfd. by Tosoh Corporation) to thereby elute an active fraction. The active fraction thus obtained is poured into an HIC-Cartridge Column (mfd. by Bio-Rad) to thereby elute an active fraction. The active fraction thus eluted is poured into a Superose 12 Column (mfd. by Pharmacia) or a Hydroxyapatite column (mfd. by Bio-Rad Laboratories) to thereby elute an active fraction. Thus three types of hyperthermophilic β-galactosidase of thus invention (E-I-1, E-I-2 and E-II) can be obtained. The enzymochemical properties of these hyperthermostable β-galactosidases are as follows.

(1) Activity

Each of E-I-1, E-I-2 and E-II has an activity of hydrolyzing lactose into galactose and glucose. Further, each of E-I-1, E-I-2 and E-II has an activity of hydrolyzing o-nitrophenyl-β-D-galactopyranoside into o-nitrophenol and galactose.

(2) Method for Determining Enzymatic Activity

In the determination of enzymatic activity, the o-nitrophenyl-β-D-galactopyranoside-hydrolyzing activity of an enzyme can be determined by spectroscopically monitoring o-nitrophenol formed via the hydrolysis of o-nitrophenyl-β-D-galactopyranoside. Namely, 5 µl of the enzyme solution of the present invention is added to a 100 mM phosphate buffer solution (pH 7.3) containing 112 mM of 2-mercaptoethanol and 1 mM of magnesium chloride to thereby give a total volume of 199 µl. Then 1 µl of a dimethyl sulfoxide solution containing 0.4 M of o-nitrophenyl-β-D-galactopyranoside is added thereto. After effecting a reaction at 95° C. for 30 minutes, the reaction is stopped by adding 100 µl of 0.1 M sodium carbonate and the absorbance of the reaction mixture at 410 nm is measured to thereby determined the amount of the o-nitrophenol thus formed. One unit of the hyperthermophilic β-galactosidase of the present invention is expressed in an amount of the enzyme whereby the absorbance at 410 nm can be increased by 1.0 at 95° C. within 1 minute. Each enzyme, E-I-1, E-I-2 and E-II, has an activity of decomposing o-nitrophenyl-β-D-galactopyranoside at pH 7.3 at 95° C., as measured above.

Further, the enzymatic activity of an enzyme of the present invention can be determined also by measuring the activity of decomposing lactose. The activity of decomposing lactose is measured by determining the amount of glucose formed by the decomposition of the substrate, as will be described hereinbelow. 5 µl of the enzyme solution is added to 70 µl of a 100 mM phosphate buffer solution (pH 7.3) containing 4 mM of magnesium sulfate. Next, 25 µl of a 2% lactose solution is added thereto and the mixture is reacted at 95° C. for 30 minutes. After stopping the reaction by cooling with ice, the amount of the liberated glucose is determined by using a glucose measurement kit Glucose B-Test Wako (mfd. by Wako Pure Chemical Industries, Ltd.). Each enzyme of the present invention, E-I-1, E-I-2 and E-II, has an activity of decomposing lactose at pH 7.5 at 95° C.

(3) Optimum Temperature

The optimum temperatures of the enzymes of the present invention, E-I-1, E-I-2 and E-II, are measured. With the use of 9.13 mU of E-I-1, 17.25 mU of E-I-2 and 11.35 mU of E-II, the activities of decomposing o-nitrophenyl-β-D-galactopyranoside are determined in accordance with the method described in item (2) above.

FIG. 1 shows the relationships between the o-nitrophenyl-β-D-galactopyranoside-decomposing activities of the enzymes, E-I-1, E-I-2 and E-II, and temperature, wherein the ordinate represents the absorbance at 410 nm of o-nitrophenol formed by the enzymatic reaction while the abscissa represents temperature (°C.), o represents E-I-1, Δ represents E-I-2, and □ represents E-II.

As FIG. 1 shows, each of the enzymes, E-I-1, E-I-2 and E-II, is active over a wide range of temperature of from 50 to 100° C. at the measurement pH value (7.3). In particular, E-I-1 shows a maximum activity at 100° C. E-I-2 and E-II each show an optimum temperature within a range of from 85 to 95° C.

Figure 2:
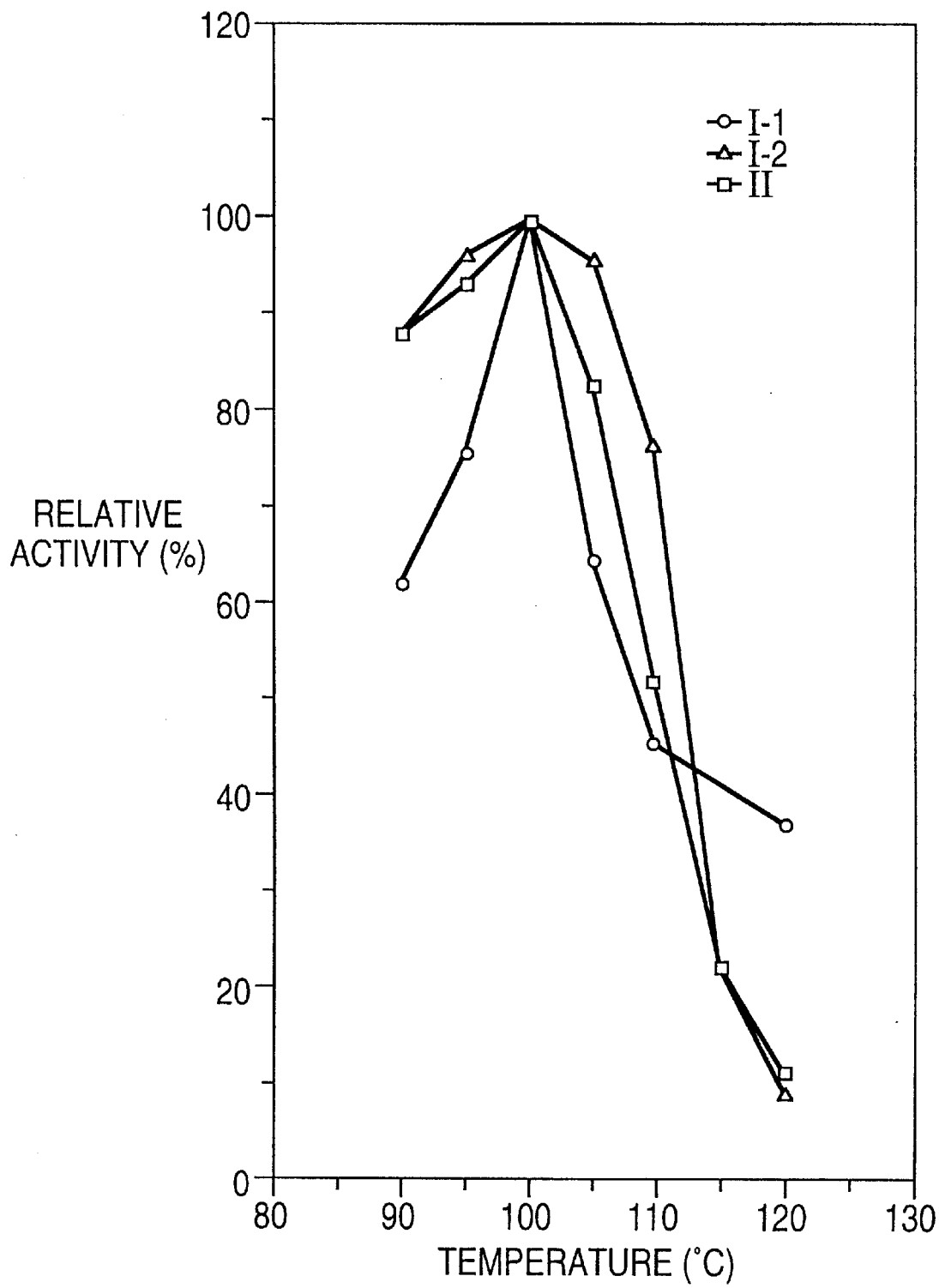
FIG. 2 is a graph showing the relationships between the activities of the enzymes of the present invention with the use of lactose as a substrate and temperature, wherein the ordinate refers to the relative activity while the abscissa refers to temperature.

Next, the optimum temperatures of the enzymes of the present invention with the use of lactose as a substrate are examined by using 45.6 mU of E-I-1, 172.5 mU of E-I-2 and 113.56 mU of E-II. The measurement is effected in accordance with the method described in item (2) above by using a 100 mM glycine-NaoH buffer solution (pH 7.5). FIG. 2 shows the relationships between the lactose-decomposing activities of the enzymes, E-I-1, E-I-2 and E-II, and temperature, wherein the ordinate represents the relative lactose-decomposing activities of E-I-1, E-I-2 and E-II calculated by taking the lactose-decomposing activity of each enzyme at 100° C. as 100%, while the abscissa represents temperature (°C.). In FIG. 2, each symbol has the same meaning as defined in FIG. 1.

As FIG. 2 shows, E-I-1, among the enzymes of the present invention, shows a maximum activity within a temperature range of from 90 to 105° C., while E-I-2 and E-II each show a maximum activity within a temperature range of from 90 to 110° C.

The reactions are carried out in a water bath (from 40 to 90° C.) and in an oil bath (from 90 to 120° C.). In particular, the reactions at a temperature exceeding 100° C. with the use of lactose as a substrate are performed in a vial provided with a screw cap so as to prevent the reaction mixture from boiling.

The optimum temperatures of the enzymes of the present invention, E-I-1, E-I-2 and E-II, are as follows.

E-I-1: 80–100° C. (using o-nitrophenyl-β-D-galactopyranoside as a substrate). 90–105° C. (using lactose as a substrate).

E-I-2: 75–95° C. (using o-nitrophenyl-β-D-galactopyranoside as a substrate). 90–110° C. (using lactose as a substrate).

E-II: 75–95° C. (using o-nitrophenyl-β-D-galactopyranoside as a substrate). 90–110° C. (using lactose as a substrate).

(4) Optimum pH Value

Figure 3:
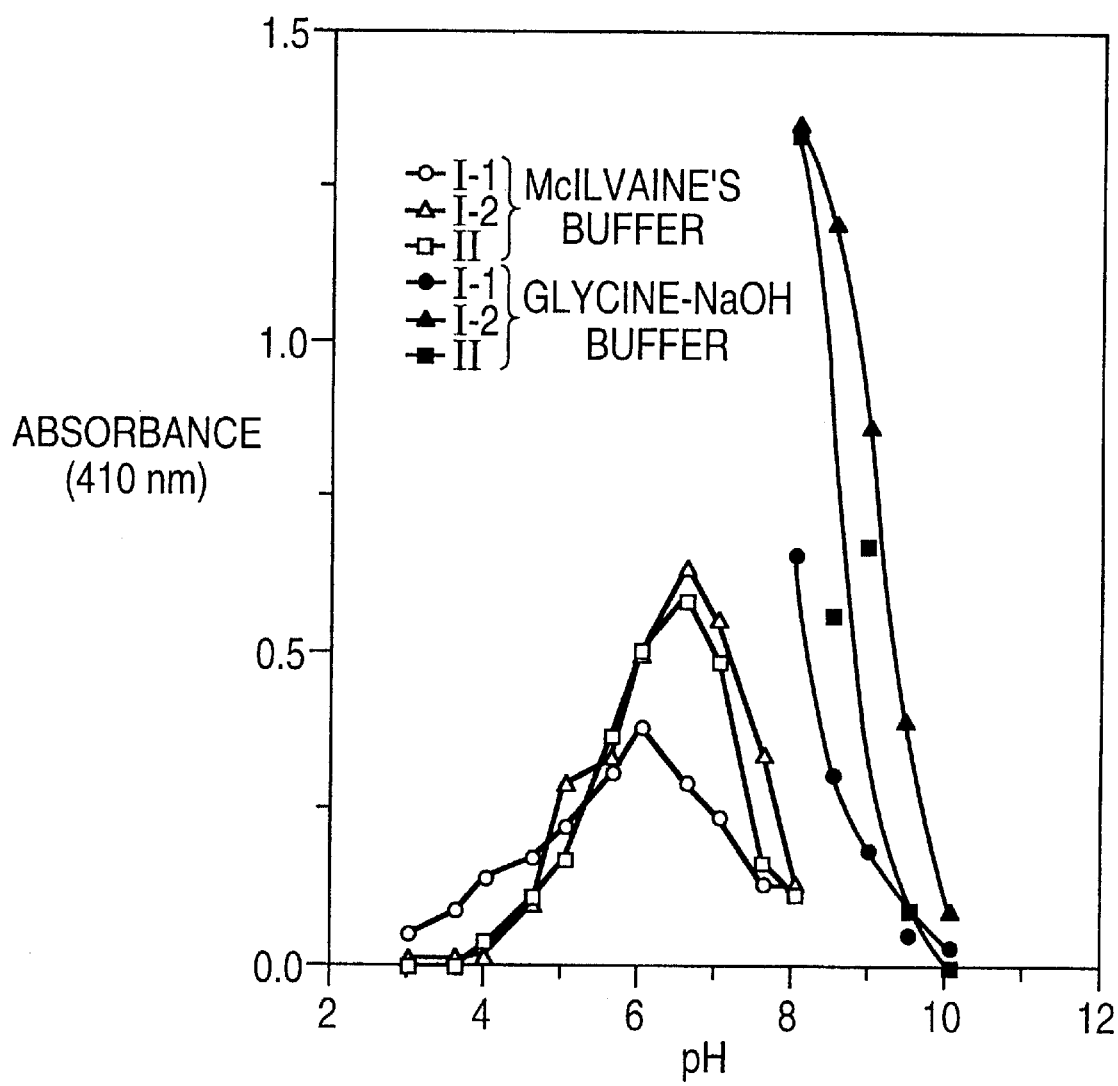
FIG. 3 is a graph showing the relationships between the activities of the enzymes of the present invention and pH, wherein the ordinate refers to the absorbance at 410 nm of the enzymatic reaction product while the abscissa refers to pH.

The optimum pH values of the enzymes, E-I-1, E-I-2 and E-II, are measured. 9.13 mU of E-I-1, 17.25 mU of E-I-2 and 11.35 mU of E-II are used. The measurement is effected by measuring o-nitrophenyl-β-D-galactopyranoside-hydrolyzing activities in accordance with the method described in item (2) above with the use of McIlvaine's buffer solution (pH 3.0 to 8.0) and a 100 mM glycine—NaOH buffer solution (pH 8.0 to 10.0). FIG. 3 shows the relationships between the o-nitrophenyl-β-D-galactopyranoside hydrolyzing activities of the enzymes, E-I-1, E-I-2 and E-II, and pH, wherein the ordinate represents the absorbance at 410 nm of o-nitrophenol formed by the enzymatic reaction while the abscissa represents pH. In FIG. 3, each symbol has the same meaning as defined in FIG. 1. Unfilled symbols show the data obtained by using McIlvaine's buffer solution and filled symbols show the data obtained by using the glycine sodium buffer solution.

As FIG. 3 shows, E-I-1 is active within a pH range of from 3.0 to 10.0 and has a maximum activity within a pH range of from 5.6 to 6.6. E-I-2 is activity within a pH range of from 3.0 to 10.0 and shows a maximum activity within a pH range of from 6.0 to 7.0. E-II is active within a pH range of from 3.0 to 10.0 and shows a maximum activity within a pH range of from 6.0 to 7.0.

The optimum pH values of the enzymes of the present invention, E-I-1, E-I-2 and E-II, are as follows.

E-I-1: pH 5.6–6.6
E-I-2: pH 6.0–7.0.
E-II: pH 6.0–7.0.
(5)Thermostability

Figure 4:
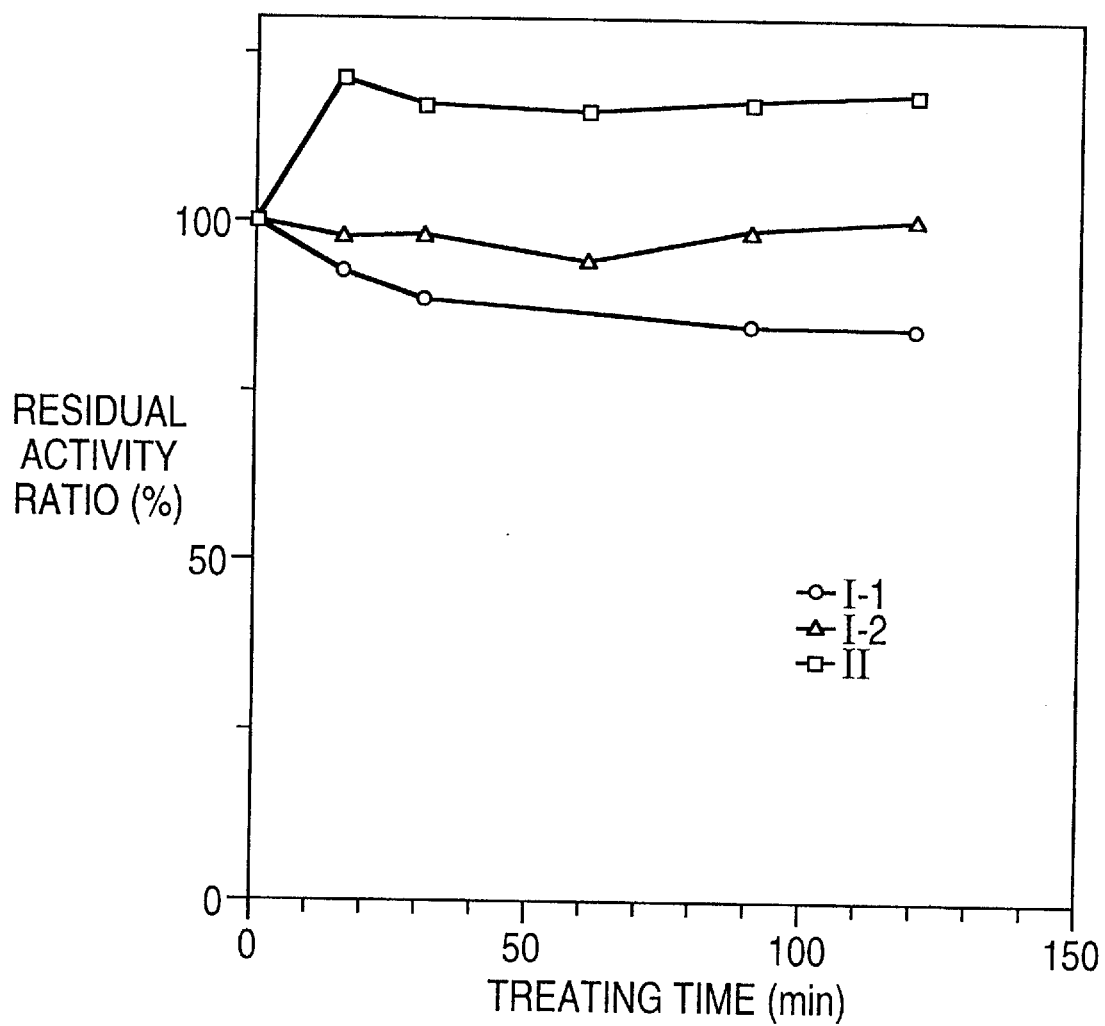
FIG. 4 is a graph showing the thermostabilities of the enzymes of the present invention, wherein the ordinate refers to the residual activity ratio while the abscissa refers to treating time.

The thermostabilities of the enzymes, E-I-1, E-I-2 and E-II, are measured. 9.13 mU of E-I-1, 17.25 mU of E-I-2 and 11.35 mU of E-II are used. The measurement is effected by treating the enzymes in 199 μl of McIlvaine's buffer solution of pH 6.0 (in the case of E-I-1) or McIlvaine's buffer solution of pH 6.6 (in the cases of E-I-2 and E-II) at 90° C. for various periods of time and then determining the o-nitrophenyl-β-D-galactopyranoside-hydrolyzing activities in accordance with the method described in item (2) above. FIG. 4 shows the thermostabilities of the enzymes, E-I-1, E-I-2 and E-II, wherein the ordinate represents the residual activity ratio (%) calculated by taking the activity of each enzyme in an untreated state as 100%, while the abscissa represents the treating time (minutes). In FIG. 4, each symbol has the same meaning as defined in FIG. 1.

As FIG. 4 shows, E-I-I has its enzymatic activity at a level of about 80% even after having been treated at 90° C. for 120 minutes. E-I-2 has almost its complete enzymatic activity after having been treated at 90° C. for 120 minutes. In the case of E-II, the enzymatic activity is not lowered but rather elevated by about 20% by having been treated at 90° C. for 120 minutes.

The thermostabilities of the enzymes of the present invention, E-I-1, E-I-2, E-II, are as follows.

E-I-1: About 80% of the activity is observed after having been treated as pH 6.0 at 90° C. for 120 minutes. After having been treated for 5 hours, about 50% of the activity is observed.

E-I-2: The activity is not lowered but sustained after having been treated at pH 6.6 at 90° C. for 120 minutes. After having been treated for 5 hours, about 90% of the activity is observed.

E-II: The activity is not lowered but rather elevated to about 120% after having been treated at pH 6.6 at 90° C. for 120 minutes. After having been treated for 5 hours, about 110 to 120% of the activity is observed.

(6) pH Stability

Figure 5:
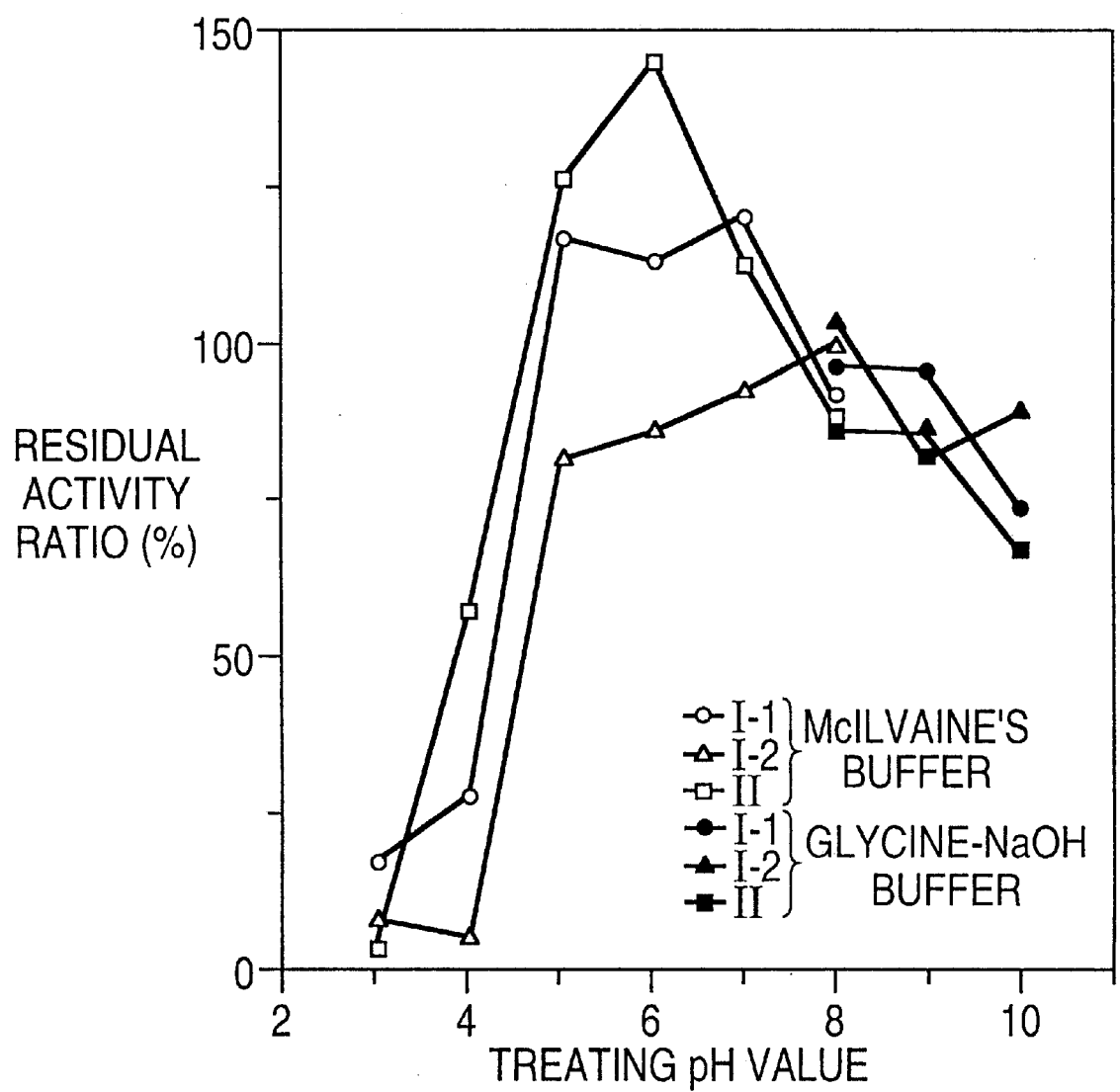
FIG. 5 is a graph showing the pH stabilities of the enzymes of the present invention, wherein the ordinate refers to the residual activity ratio while the abscissa refers to treating pH.

The pH stabilities of the enzymes of the present invention are examined. 9.13 mU of E-I-1, 34.5 mU of E-I-2 and 22.7 mU of E-II are used. McIlvaine's buffer solution is used in a pH range of from 3.0 to 8.0 and a 100 mM glycine-NaOH buffer solution is used in a pH range of from 8.0 to 10.0 To these enzymes are added 9 μl portions of the above-mentioned buffer solutions so as to give a total volume of 10 μl in each case. After having been treated at 90° C. for 30 minutes, 199 μl of McIlvaine's buffer solution of pH 6.0 (in the case of E-I-1) or 199 μl of McIlvaine's buffer solution of pH 6.6 (in the cases of E-I-2 and E-II) is added to determine the activity. The activity is determined by measuring the o-nitrophenyl-β-D-galactopyranoside-hydrolyzing activity at pH 7.3 in accordance with the method described in item (2) above. FIG. 5 shows the thermostabilities of the enzymes, E-I-1, E-I-2 and E-II, wherein the ordinate represents the residual activity ratio (%) calculated by taking the activity of each enzyme in an untreated state as 100% while the abscissa represents the treating pH value. In FIG. 5, each symbol has the same meaning as defined in FIG. 3.

As FIG. 5 shows, the enzymes of the present invention, E-I-1, E-I-2 and E-II, each remains stable within a pH range of 5.0 to 10.0 at the measurement temperature (90° C.).

E-I-1: sustains its activity after having been treated within a pH range of from 5.0 to 10.0 at 90° C. for 30 minutes.

E-I-2: sustains its activity after having been treated within a pH range of from 5.0 to 10.0 at 90° C. for 30 minutes.

E-II: sustains its activity after having been treated within a pH range of from 5.0 to 10.0 at 90° C. for 30 minutes.

(7) Substrate Specificity

Substrate specificity of the above-mentioned enzymes is determined by using p-nitrophenol-derivatives as shown in Table 1 below. The method is conducted as follows. 1485 μl of 150 mM sodium citrate buffer (pH 5.0) containing the above-mentioned enzymes is added to a quartz cuvette for a spectrophotometer. 15 μl of 0.1M substrate solution shown in Table 1 is added to the buffer and mixed. Immediately, reaction was followed to completion at 405 nm on the spectrophotometer. As a blank test, 1485 μl of 150 mM sodium citrate buffer (pH 5.0) not containing enzyme was used, and the determination described above was performed. The reaction was performed at 90° C. One unit of enzyme activity was defined as that amount required to catalyze the formation of 1 μmol p-nitrophenol.

According to the method described above, 0.028 units of E-I-1, 0.022 units of E-I-2, and 0.016 units of E-II were used. Hydrolytic activity towards p-nitrophenyl-β-D-glucopyranoside (GlcpβNp), p-nitrophenyl-β-D-galactopyranoside (GalpβNp), p-nitrophenyl-β-D-mannopyranoside (ManpβNp), p-nitrophenyl-β-D-xylopyranoside (XylpβNp), p-nitrophenyl-β-D-fucopyranoside (FucpβNp), and p-nitrophenyl-α-D-galactopyranoside (GalpαNp), was determined.

Results are shown in Table 1. Table 1 shows the specific activity of the above-mentioned enzymes, E-I-1, E-I-2, and E-II, towards the above-described substrates and their relative activities at 90° C. and pH 5.0.

TABLE 1

Specific activity of the β-galactosidases

| Substrate | E-I-1 Specific activity U/mg | E-I-1 Relative activity % | E-I-2 Specific activity U/mg | E-I-2 Relative activity % | E-II Specific activity U/mg | E-II Relative activity % |
|---|---|---|---|---|---|---|
| GlcpβNp | 0.776 | 100 | 32.3 | 100 | 44.6 | 100 |
| GalpβNp | 0.694 | 89.4 | 12.3 | 38.1 | 19.4 | 43.6 |
| ManpβNp | 0 | 0 | 54.8 | 169.4 | 3.3 | 7.5 |
| XylpβNp | 0 | 0 | 4.2 | 13.1 | 5.4 | 12.0 |
| FucpβNp | 0 | 0 | 0 | 0 | 0 | 0 |
| GalpαNp | 0 | 0 | 0 | 0 | 0 | 0 |

Suitable selection of an above-mentioned enzyme, E-I-1, E-I-2, or E-II, is capable of optimal reaction towards a target substrate.

A genetic engineering process for producing a hyperthermostable β-galactosidase according to the invention comprises:

(a) constructing a plasmid in which an isolated DNA encoding a hyperthermophilic β-galactosidase as claimed in any of the first invention to the third invention is inserted;

(b) transforming an appropriate host organism with the plasmid; and (c) cultivating the transformed host organism and recovering the hyperthermostable β-galactosidase from the culture.

The hyperthermostable β-galactosidase gene which includes an isolated DNA encoding a hyperthermophilic β-galactosidase of this invention can be screened and obtained by the expression cloning method using cosmid vectors. Expression cloning is a method which can be used for cloning of the gene coding some enzymes without any information about the primary structure of the target enzyme. For example, a pullulanase gene of *Pyrococcus furiosus* (WO 92/02614) is cloned using the expression cloning method. However, the method cannot be applied to cloning every type of enzyme because when a plasmid vector is used for the method, a suitable restriction enzyme is needed. It must cleave the target gene into a small enough size to be inserted in a plasmid vector and not cleave the target gene inside. Furthermore, the method is complicated because it needs a number of clones.

Subsequently, the present inventors have attempted to isolate the β-galactosidase gene by screening β-galactosidase activities in a cosmid library constructed with *Pyrococcus furiosus* genomic DNA and the cosmid vectors in which larger DNA fragments (35–50 kbp) can be inserted than in plasmid vectors. By using cosmid vectors, dangers for cleaving the target gene encoding the enzyme by a restriction enzyme decrease and the numbers of clones necessary to test can be reduced. On the other hand, enzyme activity may not be detected because of low expression of the enzyme since the cosmid vectors have less copy numbers in host organisms than plasmid vectors.

The present inventors observed an extremely high thermostability of the target enzyme and combined a process of cultivating the transformants in the cosmid library individually with a process of preparing the lysates which contain only the thermostable proteins. The group of these lysates is named "cosmid protein library". By using the library for detection of the enzyme activity, detection sensitivity increases over when using colonies of the transformants and bad influences such as background by proteins from hosts or inhibition of enzyme activity can be eliminated.

The present inventors isolated several cosmid clones which show β-galactosidase activity by screening the cosmid protein library constructed with *Pyrococcus furiosus* genomic DNA. The inventors searched the cosmid protein library derived from *Pyrococcus furiousus*, and obtained one cosmid clone exhibiting a β-galactosidase activity, though weak, in the presence of 1% SDS. Furthermore, the present inventors isolated the gene encoding a hyperthermostable β-galactosidase from the DNA fragments inserted in the clones isolated above by making full use of various genetic engineering techniques, and determined the DNA sequence of the gene. Moreover, the present inventors succeeded in the expression of the hyperthermostable β-galactosidase with the use of the gene, thus completing the present invention.

By the way, the expression cloning method using cosmid vectors which is described here cannot always be applied to any thermostable enzyme. The result is determined by the property of the target gene. For example, the present inventors attempted to isolate the gene encoding a protease (α-glucosidase) of *Pyrococcus furiosus* [*Appl. Env. Microbiol.* 56, 1992–1998 (1990); *Journal of Bacteriology,* 172, 3654–3660 (1990)], but they were unable to isolate the gene.

The microorganism to be used in the present invention is not particularly restricted, so long as it can produce a hyperthermostable β-galactosidase gene. For example, strains belonging to the genus Pyrococcus, i.e., hyperthermostable bacteria, such as *Pyrococcus furiosus* DMS 3638 *Pyrococcus woesei* DMS 3773 are usable therefor. These strains are both available from Deutsche Sammlung von Mikroorganismen und Zellkulturen GmbH.

For example, a cosmid library of *Pyrococcus furiosus* gene can be prepared in the following manner. First, the genome of *Pyrococcus furiosus* 3638 is partially digested by using an appropriate restriction enzyme, for example, Sau 3AI (mfd. by Takara Shuzo Co., Ltd.). After fractionating according to the size of 35 to 50 kbp, each DNA fragment thus obtained is ligated with an appropriate cosmid vector, for example, Triple Helix Cosmid Vector (mfd. by Stratagene). The *Pyrococcus furiosus* genome DNA fragments are first packaged in λ-phage particles by the in vitro packaging method and then an appropriate *Escherichia coli* strain, for example, *E. coli* DH5αMCR (mfd. by BRL) is transformed with the obtained phage solution to thereby give the desired cosmid library. Then cosmid DNAs are prepared from several colonies of the transformant and the insertion of the genome DNA fragments of 35 to 50 kbp into the transformant is thus confirmed. In general, 300 to 700 colonies may be incubated.

After the completion of the incubation of each colony, the incubated cells are collected. The cells are processed to the cosmid protein libraries by treating at 100° C. for 10 minutes, sonicating, and treating at 100° C. for 10 minutes once more. Then the β-galactosidase activity in the lysates obtained is determined (optionally in the presence of 1% SDS), whereby colonies expressing a hyperthermostable β-galactosidase which remain stable after the above treatment can be screened. The β-galactosidase activity is determined by, for example, using o-nitrophenyl-β-D-galactopyranoside or lactose (mfd. by Nacalai Tesque) as a substrate at a reaction temperature of, for example, 95° C. Next, the fragment inserted into the cosmid DNA of transformants showing activity is analyzed.

Inserted fragments in the cosmid DNAs of seven active transformants, among 500 transformants prepared by the present inventors, contain an EcoRI fragment of about 2.2 kbp in common. Thus this common DNA fragment is prepared to examine its properties. For example, a cosmid DNA expressing the activity is completely digested with a restriction enzyme EcoRI (mfd. by Takara Shuzo Co., Ltd.) and electrophoresed on a gel to thereby purify the target EcoRI DNA fragment of about 2.2 Kbp. Then the obtained fragment is inserted into the EcoRI site of an appropriate vector, for example, pUC19 (mfd. by Takara Shuzo Co., Ltd.). Thus a plasmid holding the common DNA fragment, which has been named pTGE-101 by the present inventors, can be prepared.

By this plasmid pTGE-101, an appropriate *Escherichia coli* strain such as *E. coli* JM109 is transformed. Thus a transformant named *Escherichia coli* JM109/pTGE-101 by the present inventors can be obtained. After incubating this *E. coli* transformant, the cells are collected and the β-galactosidase activity of the protein expressed in the cells is determined. The activity can be determined in the following manner. Namely, the cells and disrupted cells, which have been either thermally treated at 100° C. for 10 minutes, twice or untreated, are used and the above-mentioned o-nitrophenyl-β-D-galactopyranoside is employed as a substrate to effect a reaction at 70° C. or 95° C., whereby the thermostability of the expressed protein can be examined.

As Table 2 below shows, a gene coding for a thermostable β-galactosidase, which is inactivated when treated at 100° C. for 10 minutes twice but exhibits its activity at a reaction temperature of 70° C., has been inserted into pTGE-101.

TABLE 2

| Thermal treatment (100° C., 10 minutes, twice) | Reaction 70° C. | temperature 95° C. |
| --- | --- | --- |
| Treated | − | − |
| Untreated | + | − |

In Table 2, symbol (+) indicates the presence of β-galactosidase activity, while symbol (−) indicates the absence thereof.

Figure 6:
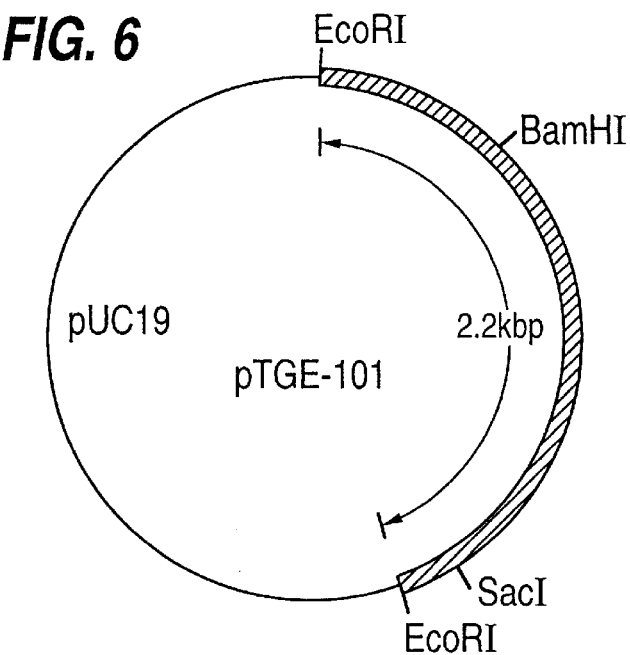
FIG. 6 shows a restriction enzyme map of plasmid pTGE-101.

FIG. 6 shows a restriction enzyme map of the plasmid pTGE-101 wherein a thick solid line represents the EcoRI DNA fragment of about 2.2 kbp inserted into the plasmid pUC19. This fragment codes for the thermostable β-galactosidase. This fragment further codes for a part of the target hyperthermostable β-galactosidase.

The above-mentioned EcoRI DNA fragment of about 2.2 kbp is labeled. By using the labeled DNA fragment thus obtained as a probe, DNA fragments, which have been obtained by completely digesting cosmids having a hyperthermostable β-galactosidase gene with a restriction enzyme Hind III (mfd. by Takara Shuzo Co., Ltd.) and separating by agarose gel electrophoresis, are subjected to Southern hybridization. Thus a Hind III DNA fragment (about 3.3 kbp) hybridized with the probe can be identified. Then this fragment is extracted from the agarose gel and inserted into the Hind III site of an appropriate vector, for example, pUC19. Thus a plasmid, named pTGH-301 by the present inventors, can be prepared. By transforming E. coli JM109 with this plasmid, a transformant, named Escherichia coli JM109/pTGH-301 by the present inventors, can be obtained. This transformant is incubated and after completion of the incubation the cells are collected. The β-galactosidase expressed in these cells remains stable after treating at 100° C. for 10 minutes twice. Thus the target hyperthermostable β-galactosidase has been expressed therein.

Figure 7:
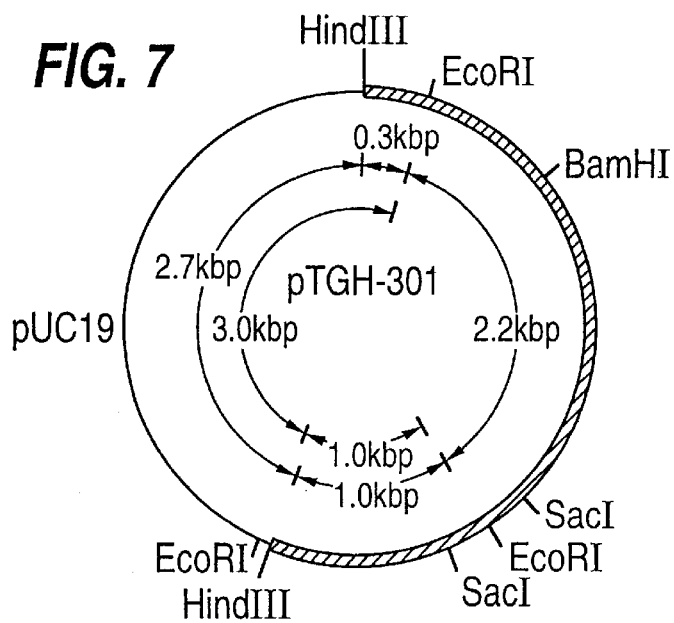
FIG. 7 shows a restriction enzyme map of plasmid pTGH-301.

FIG. 7 shows a restriction enzyme map of the plasmid pTGH-301 wherein a thick solid line represents the Hind III DNA fragment of about 3.5 kbp inserted into the plasmid pUC19. This fragment contains a hyperthermostable β-galactosidase gene. This fragment also contains the EcoRI DNA fragment of about 2.2 kbp shown in FIG. 6.

A part of the DNA sequence coding for the hyperthermostable β-galactosidase which is contained in plasmid pTGH-301 is shown in SEQ ID NO. 2 of the Sequence Listing. SEQ ID NO. 1 of the Sequence Listing shows the amino acid sequence deduced from the DNA sequence shown in SEQ ID NO. 2. Namely, SEQ ID NO. 1 of the Sequence Listing is the amino acid sequence of the hyperthermostable β-galactosidase which is produced with the use of an isolated DNA encoding a hyperthermostable β-galactosidase of the present invention. The isolated DNA encoding a hyperthermostable β-galactosidase of the present invention is also provided as an isolated DNA which has a DNA sequence encoding the amino acid sequence shown in SEQ ID NO. 1 of the Sequence Listing consisting of any combinations of genetic codes selected from degenerate codons.

Namely, the DNA sequence shown in SEQ ID NO. 2 of the Sequence Listing is an example of the hyperthermostable β-galactosidase gene given in the present invention.

Moreover, the N-terminal amino acid sequence of the purified sample of the hyperthermostable β-galactosidase produced by Escherichia coli JM109/pTGH301 agreed with the N-terminal amino acid sequence of the amino acid sequence shown in SEQ ID NO. 1 of the Sequence Listing.

From this plasmid pTGH-301, a Hind III-EcoRI DNA fragment (about 1.0 kbp) free from the hyperthermostable β-galactosidase gene can be eliminated in the following manner.

Namely, from three types of DNA fragments obtained by digesting the plasmid pTGH-301 with EcoRI, only one of about 1.0 kbp is eliminated and ligation is effected, followed by transduction into E. coli JM109. Then the hyperthermostable β-galactosidase activities of the obtained colonies are determined and a plasmid is prepared from a colony showing an activity.

The plasmid is named pTGEH-401, while E. coli JM109 transformed by this plasmid is named Escherichia coli JM109/pTGEH-401, and is deposited at the National Institute of Bioscience and Human-Technology Agency of Industrial Science and Technology, Japan, under the accession number of FERM BP-4468.

Figure 8:
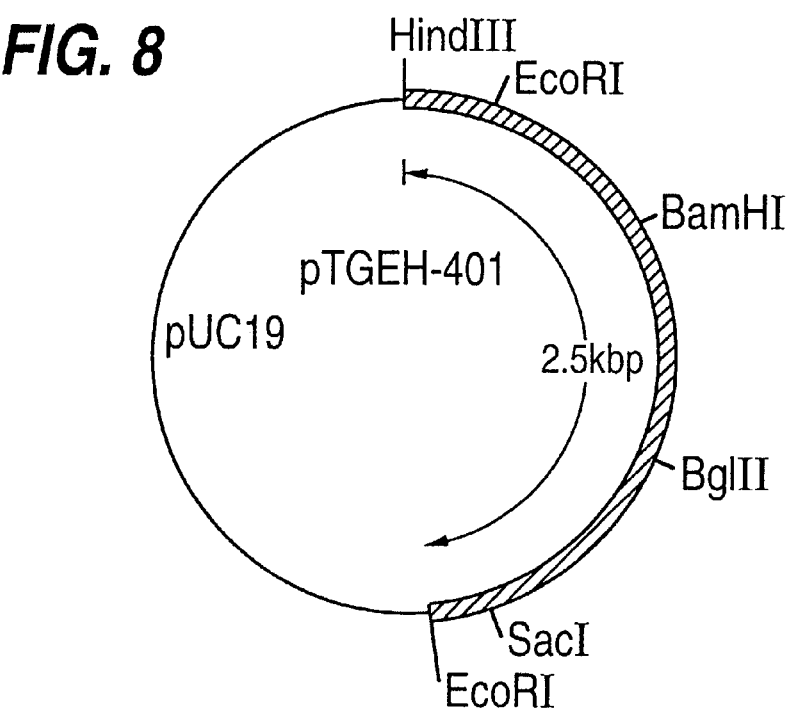
FIG. 8 shows a restriction enzyme map of plasmid pTGEH-401.

FIG. 8 shows a restriction enzyme map of the plasmid pTGEH-401, wherein a thick solid line represents the DNA fragment inserted into the plasmid pUC19.

Figure 9:
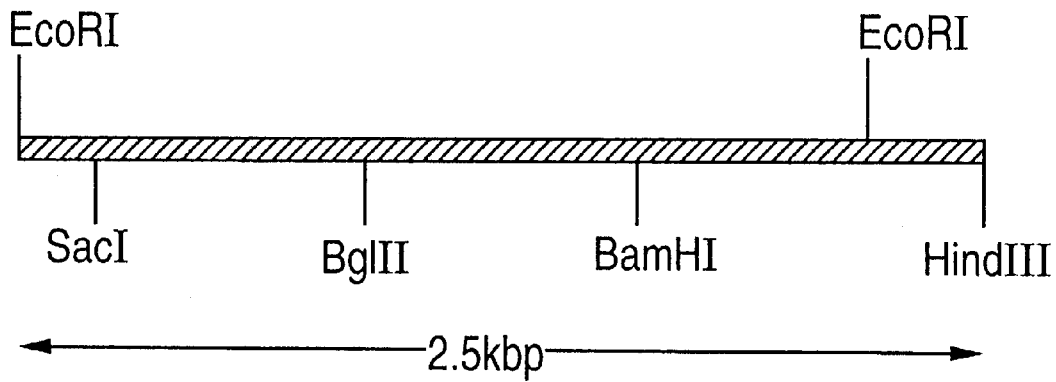
FIG. 9 shows a restriction enzyme map of one example of a hyperthermophilic β-galactosidase gene of the present invention.

FIG. 9 shows a restriction enzyme map of a DNA fragment originating in Pyrococcus furiosus which has been inserted into the plasmid pTGEH-401. Namely, FIG. 9 shows the restriction enzyme map of one example of the hyperthermostable β-galactosidase gene obtained according to the present invention.

When a transformant constructed by transducing a recombinant plasmid containing a hyperthermostable β-galactosidase gene such as Escherichia coli JM109/pTGH-301 or Escherichia coli JM109/pTGEH-401 is incubated, the hyperthermostable β-galactosidase is accumulated in the culture. The hyperthermostable β-galactosidase can be purified from this culture by, for example, harvesting the cells, disrupting the cells by ultrasonication and treating the supernatant obtained by centrifuging with a combination of purification procedures such as gel filtration chromatography, ion exchange chromatography and hydrophobic chromatography.

When the hyperthermostable β-galactosidase is to be purified in the present invention, in particular, it is advantageous to thermally treat the cells either before or after the ultrasonication, since the contaminating proteins are denatured thereby and thus the purified can be easily carried out.

The hyperthermostable β-galactosidase obtained by expressing a gene of the present invention, for example, a gene integrated in the plasmid pTGH-301 has the following physicochemical properties.

(1) Activity and Substrate Specificity

It has an activity of hydrolyzing lactose into galactose and glucose. Further, it has an activity of hydrolyzing o-nitrophenyl-β-D-galactopyranoside into o-nitrophenol and galactose.

(2) Method for Determining Enzymatic Activity

[(2)-a]

In the determination of enzymatic activity, the o-nitrophenyl-β-D-galactopyranoside-hydrolyzing activity of an enzyme can be determined by spectroscopically monitoring o-nitrophenol formed via the hydrolysis. Namely, 5 μl of the enzyme solution of the present invention is added to 199 μl of a 100 mM phosphate buffer solution (pH 7.3) containing 112 mM of 2-mercaptoethanol and 1 mM of magnesium chloride. Then 1 μl of a dimethyl sulfoxide solution containing 0.4 M of o-nitrophenyl-β-D-galactopyranoside is added thereto. After effecting a reaction at 95° C. for 30 minutes, the reaction is stopped by adding 100 μl of 0.1 M sodium carbonate and the absorbance of the reaction mixture at 410 nm is measured to thereby determine the amount of the o-nitrophenol thus formed. One unit of the hyperthermostable β-galactosidase obtained in accordance with the present invention is expressed in an amount of the enzyme whereby the absorbance at 410 nm can be increased by 1.0 at 95° C. within 1 minute. The enzyme obtained in the present invention has an activity of decomposing o-nitrophenyl-β-D-galactopyranoside at pH 7.3 at 95° C., as measured above.

[(2)-b]

The o-nitrophenyl-β-D-galactopyranoside-hydrolyzing activity of the β-galactosidase also can be determined by the following method. The enzyme reaction was started by adding 15 μl of a dimethyl sulfoxide solution containing 1 M of o-nitrophenyl-β-D-galactopyranoside into 1485 μl of McIlvaine's buffer solution containing the enzyme which is in a quartz cuvette for a spectrophotometer to give a final concentration of o-nitrophenyl-β-D-galactopyranoside of 10 mM. Reaction was detected by monitoring change of absorbance at 410 nm versus time on the spectrophotometer. Based on the change of absorbance at 410 nm per minute, o-nitrophenol released per minute was calculated by using an absorbance coefficient determined previously. One unit of enzyme activity was defined as that amount required to catalyze the release of 1 μmol o-nitrophenol per minute. Protein determination of the enzyme protein was performed by the method of Lowry's.

[(2)-c]

Further, the enzymatic activity of the enzyme obtained in the present invention can be determined also by measuring the activity of decomposing lactose. The activity of decomposing lactose is measured by determining the amount of glucose formed by the decomposition of the substrate, as will be described hereinbelow. 5 μl of the enzyme solution is added to 70 μl of a 100 mM glycine sodium buffer solution (pH 7.5) containing 4 mM of magnesium sulfate. Next, 25 μl of a 2% lactose solution is added thereto and the mixture is reacted at 95° C. for 30 minutes. After stopping the reaction by cooling with ice, the amount of the liberated glucose is determined by using a glucose measurement kit Glucose B-Test Wako (mfd. by Wako Pure Chemical Industries, Ltd.). The enzyme obtained in the present invention has an activity of decomposing lactose at pH 7.5 at 95° C.

(3) Thermostability

By using 32 mU of the enzyme obtained in the present invention, the thermostability of the enzyme is measured. The measurement is effected by determining the o-nitrophenyl-β-D-galactopyranoside-hydrolyzing activity of the enzyme in accordance with the method described in item (2) above except that the phosphate buffer solution is replaced by McIlvaine's buffer solution (pH 6.6) containing 112 mM of 2-mercapto-ethanol and 1 mM of $MgCl_2$. After treating the enzyme in 204 μl of the above-mentioned buffer solution at 90° C. for various periods of time, 1 μl of a dimethyl sulfoxide solution containing 0.4 M of o-nitrophenyl-β-D-galactopyranoside is added, followed by a reaction at 95° C. for 30 minutes. Then the reaction is stopped by adding 100 μl of 0.1 M sodium carbonate and the absorbance at 410 nm is measured to thereby determine the amount of the o-nitrophenol thus formed.

The enzyme obtained in the present invention exhibits a hyperthermostability and suffers from no decrease in enzymatic activity even after treating at 90° C. for 120 minutes.

The thermostability of the β-galactosidase was determined in accordance with the method described in [(2)-b]. 1 ml of McIlvaine's buffer solution containing the enzyme (pH 5.0) was incubated at 90° C. and aliquots were withdrawn at appointed times. The enzyme reaction was started by adding 10 μl of the aliquot to 1490 μl of McIlvaine's buffer solution (pH 5.0) containing 10 mM of o-nitrophenyl-β-D-galactopyranoside which had been incubated at 90° C. in the cuvette. Reaction was detected by monitoring absorbance at 410 nm versus time with a spectrophotometer. Based on the change of absorbance at 410 nm per minute, o-nitrophenol released per minute was calculated by using the absorbance coefficient determined previously. One unit of enzyme activity was defined as that amount required to catalyze the release of 1 μmol o-nitrophenol per minute.

Figure 10:
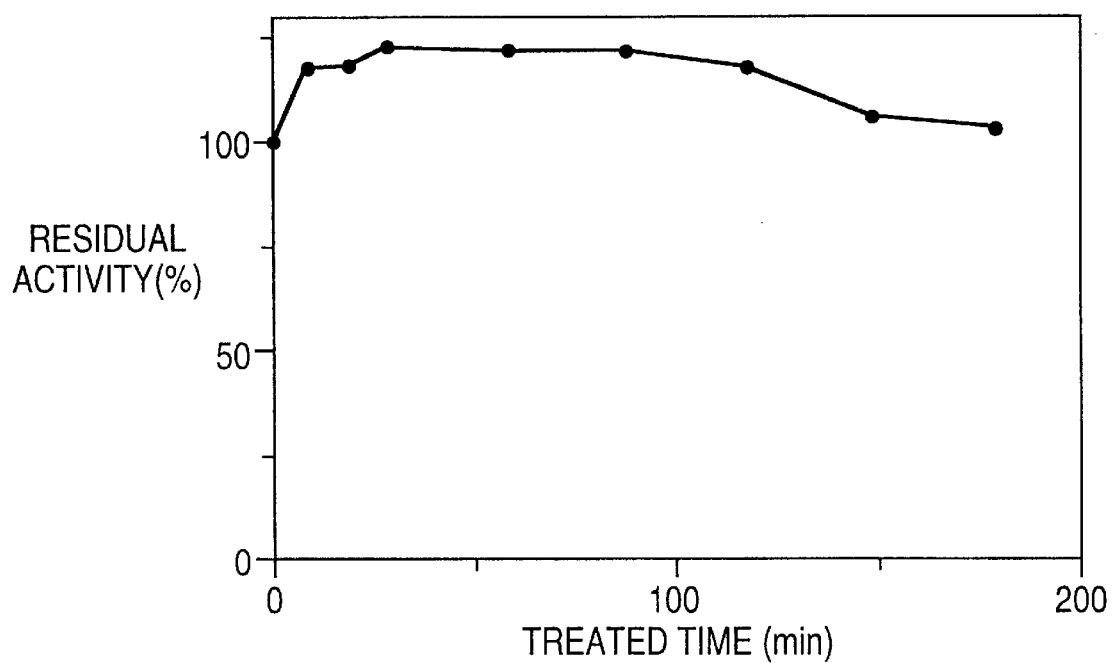
FIG. 10 is a graph showing the thermostability of a hyperthermophilic β-galactosidase of the present invention.

As FIG. 10 shows, about 100% of the activity of the β-galactosidase was retained even after treating at 100° C. for 150 min. FIG. 10 is a graph showing the thermostability of β-galactosidase wherein the ordinate represents the residual activity ratio (%), while the abscissa represents the treating time (minutes) at 90° C.

(4) Optimum pH Value

Figure 11:
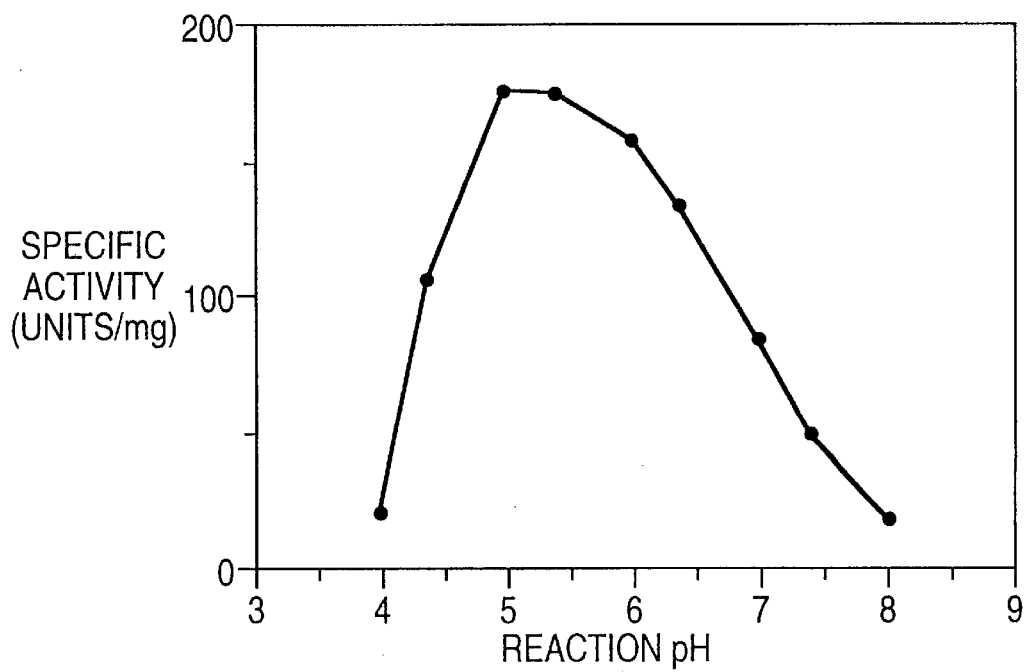
FIG. 11 is a graph showing the optimum pH of a hyperthermophilic β-galactosidase of the present invention.

The optimum pH value of the β-galactosidase was measured in accordance with the method described in [(2)-b] above. 1490 μl of McIlvaine's buffer solution which was determined to have its appointed pH value (pH 4–8) and containing 10 mM of o-nitrophenyl-β-D-galactopyranoside was incubated at 90° C. in the cuvette and the enzyme reaction was started by adding 10 μl of McIlvaine's buffer solution (pH 5.0) containing the enzyme into the cuvette. Reaction was detected by monitoring the change of absorbance at 410 nm versus time with a spectrophotometer. Change of absorbance at 410 nm per minute was determined. Based on the change of absorbance at 410 nm per minute, o-nitrophenol released per minute was calculated by using the absorbance coefficient determined at each pH condition. One unit of enzyme activity was defined as that amount required to catalyze the release of 1 μmol o-nitrophenol in a minute. As shown in FIG. 11, the β-galactosidase shows its maximum activity at a pH range of from 4.5 to 6.5. FIG. 11 is a graph showing the optimum pH value of the β-galactosidase wherein the ordinate represents the specific activity (units/mg protein), while the abscissa represents treating pH.

(5) Optimum Temperature

Figure 12:
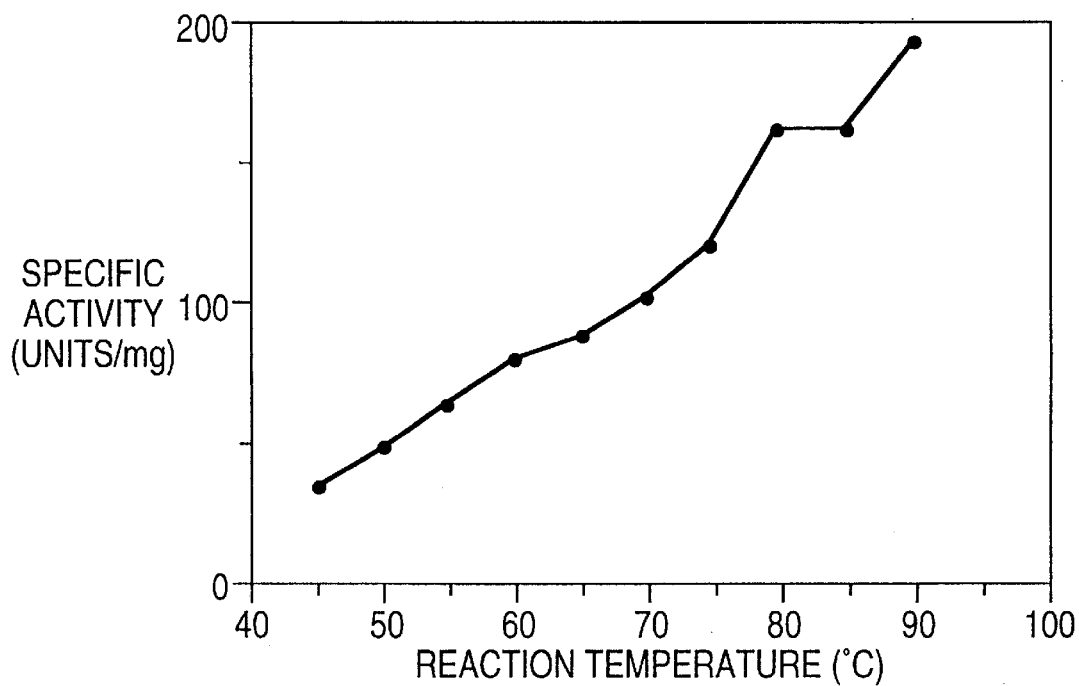
FIG. 12 is a graph showing the optimum temperature of a hyperthermophilic β-galactosidase of the present invention.

The optimum temperature of the β-galactosidase was measured in accordance with the method described in [(2)-b]. 1485 μl of McIlvaine's buffer solution (pH 5.0) containing the β-galactosidase was incubated at the appointed temperature (45° C.–90° C.) in the cuvette and the enzyme reaction was started by adding 15 μl of a dimethyl sulfoxide solution containing 1 M of o-nitrophenyl-β-D-galactopyranoside to give the final concentration of n-nitrophenyl-β-D-galactopyranoside to 10 mM. Reaction was detected by monitoring change of absorbance at 410 nm versus time with a spectrophotometer. Change of absorbance at 410 nm per minute was determined. Based on the change of absorbance at 410 nm per minute, o-nitrophenol released per minute was calculated by using the absorbance coefficient determined at each temperature. One unit of enzyme activity was defined as that amount required to catalyze the release of 1 μmol o-nitrophenol per minute. As FIG. 12 shows, the β-galactosidase shows its maximum activity above 90° C. FIG. 12 is a graph showing the optimum temperature of the β-galactosidase wherein the ordinate represents the specific activity (units/mg protein), while the abscissa represents treating temperature (° C.).

(6) pH Stability

The pH stability of the β-galactosidase is determined in accordance with the method described in [(2)-b]. 1485 μl of McIlvaine's buffer solution containing 20 units/ml of the β-galactosidase was incubated at the appointed pH (pH 3–8) for 10 minutes at 90° C. To start the reaction, 10 μl of aliquot of the enzyme solution was added to 1490 μl of McIlvaine's buffer solution (pH 5.0) which contained 10 mM of o-nitrophenyl-β-D-galactopyranoside and was preincubated at 90° C.

Figure 13:
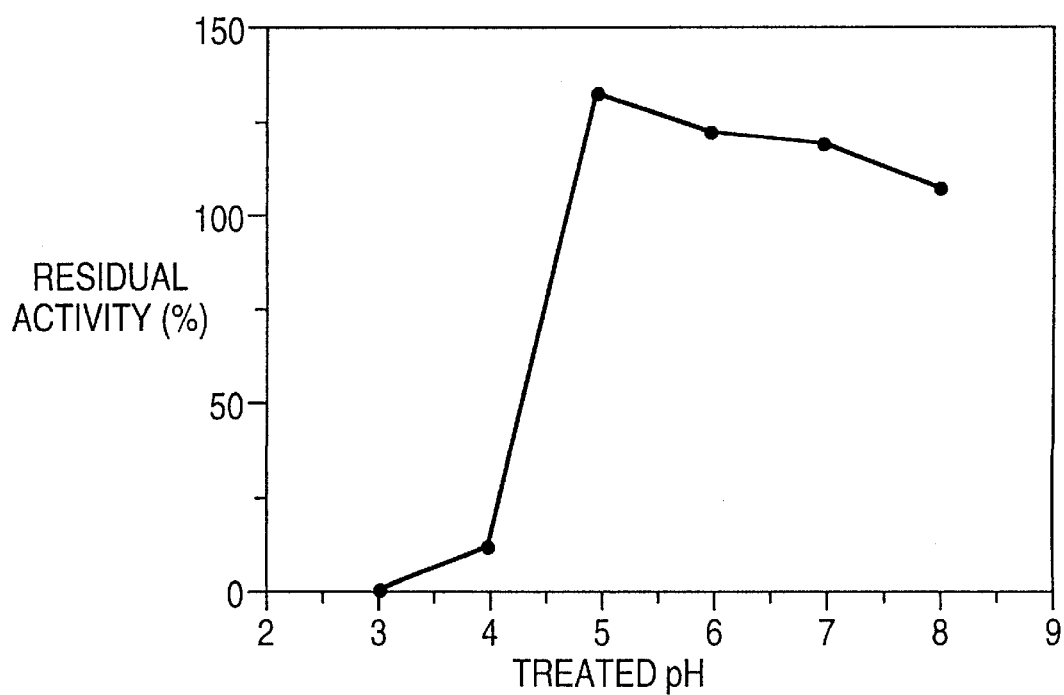
FIG. 13 is a graph showing the pH stability of a hyperthermophilic β-galactosidase of the present invention.

Reaction was detected by monitoring the change of absorbance at 410 nm versus time with a spectrophotometer. Change of absorbance at 410 nm in a minute was determined. Based on the change of absorbance at 410 nm per minute, o-nitrophenol released per minute was calculated by using the absorbance coefficient determined previously. One unit of enzyme activity was defined as that amount required to catalyze the release of 1 μmol o-nitrophenol in a minute. As FIG. 13 shows, the β-galactosidase sustains its activity even after treating within a pH range of from 4.5 to 8.0 at 90° C. for 10 minutes. FIG. 13 is a graph showing the optimum pH value of the β-galactosidase wherein the ordinate represents the residual activity ratio (%), while the abscissa represents treating pH.

(7) Substrate Specificity

Substrate specificity of the β-galactosidase can be determined by using p-nitrophenol derivatives as shown in Table 3 below. The method is conducted as follows. 1485 μl of 150 mM sodium citrate buffer solution (pH 5.0) containing the β-galactosidase is added to a quartz cuvette for a spectrophotometer. 15 μl of 0.1M substrate solution shown in Table 1 is added to the enzyme solution and mixed. Immediately, reaction was detected by monitoring the change of absorbance at 410 nm versus time with a spectrophotometer. As a blank test, 1485 μl of 150 mM sodium citrate buffer (pH 5.0) not containing enzyme was used, and the determination described above was performed. In the test, reaction was performed at 90° C. One unit of enzyme activity was defined as that amount required to catalyze the release of 1 μmol p-nitrophenol per minute.

According to the method described above, hydrolytic activity towards p-nitrophenyl-β-D-glucopyranoside (GlcpβNp), p-nitrophenyl-β-D-galactopyranoside (Galp6'Np), p-nitrophenyl-β-D-mannopyranoside (ManpβNp), p-nitrophenyl-β-D-xylopyranoside (XylpβNp), p-nitrophenyl-β-D-fucopyranoside (FucpβNp), and p-nitrophenyl-α-D-galactopyranoside (GalpαNp), was determined.

Results are shown in Table 3, which shows specific activity (units/mg protein) of the β-galactosidase towards the above-described substrates and relative activity (%).

TABLE 3

Specific activity of the β-galactosidase

| Substrate | Specific activity U/mg | Relative activity % |
|---|---|---|
| GlcpβNp | 79.2 | 100 |
| GalpβNp | 28.8 | 36.4 |
| ManpβNp | 131.2 | 165.7 |
| XylpβNp | 10.5 | 13.2 |
| FucpβNp | 0 | 0 |
| GalpαNp | 0 | 0 |

Substrate specificity of the β-galactosidase was also determined by using the natural substrate as shown in Table 4 below. The method is conducted as follows. Each substrate as shown in Table 4 was dissolved in 2 ml of 150 mM sodium citrate buffer (pH 5.0) so as to give a final concentration equivalent to 17 g/l for carboxymethyl-cellulose, avicel, or laminarin, and to 50 mM for the other substrates. After incubating these solutions at 90° C., 5 μl of phosphate buffer (pH 5.0) containing the β-galactosidase was added and the reaction was performed at 90° C. for 5 minutes. After stopping the reaction by cooling with ice, the amount of the liberated glucose was determined by using a glucose measurement kit Glucose C-Test Wako (mfd. by Wako Pure Chemical Industries, Inc.) One unit of enzyme activity was defined as that amount required to catalyze the hydrolysis of 1 μmol of the substrate in a minute. Results are shown in Table 4.

TABLE 4

Substrate specificity of the β-galactosidase

| Substrate | Relative activity % |
|---|---|
| Lactose | 100 |
| Cellobiose | 209.3 |
| β-methyl-D-glucoside | 6.5 |
| Salicin | 89.0 |
| Arbutin | 4.5 |
| Sucrose | 0 |
| Maltose | 0 |
| Carboxymethyl-cellulose | 0 |
| Avicel | 0 |
| Laminarin | 0 |

SDS-Resistant β-Galactosidase

The fragments inserted into the cosmid DNA of one transformant having exhibited an activity among 500 transformants prepared by the inventors are cleaved with the use of various restriction enzymes, and the resultant fragment group is inserted into a suitable vector. For example, the cosmid DNA prepared from the above-mentioned cosmid clone is digested with Hind III (manufactured by Takara Shuzo Co., Ltd.), and the obtained DNA fragments are inserted into the Hind III site of the plasmid vector pUC18 (manufactured by Takara Shuzo Co., Ltd.). Thus a recombinant plasmid can be obtained.

Subsequently, this recombinant plasmid is introduced into the Escherichia coli JM109 (manufactured by Takara Shuzo Co., Ltd.) to thereby obtain a transformant, which is cultured and harvested. The activity of the β-galactosidase, a protein expressed in the cells, is assayed. The assay is conducted with respect to the cells and lysate thereof having undergone heat treatment at 100° C. for 10 minutes twice by using o-nitrophenyl-β-D-galactopyranoside as a substrate in the presence of 1% SDS. The activity is assayed by conducting the reaction at 95° C. for 30 minutes.

The above transformant lysate has no activity recognized. Then, the activity search was conducted in the same manner with the use of each of the restriction enzymes Acc I, Bgl II, Eco RV, Pst I and Hinc II (all manufactured by Takara Shuzo Co., Ltd.), but no activity was found.

The same search was conducted with the use of restriction enzyme capable of providing longer DNA fragments than with the use of the above restriction enzymes, for example, Cla I (manufactured by Takara Shuzo Co., Ltd.). However, deletion was found in the insert fragments at the stage of insertion into the plasmid, and no activity was recognized. Next, the search was conducted in the same manner with the use of Sma I (manufactured by Takara Shuzo Co., Ltd.). As a result, activity was recognized in a plasmid having a DNA fragment of about 4 kbp inserted therein. This plasmid was designated plasmid pTG2S-112 by the inventors. By transforming Escherichia coli JM109 by this plasmid, a transformant designated as Escherichia coli JM109/pTG2S-112 by the present inventors can be obtained. This transformant is incubated and, after the completion of the incubation, the cells are collected. The β-galactosidase expressed in these cells remains stable irrespective of heat treating in the presence of 1% SDS at 100° C. for 10 minutes twice. Thus the target hyperthermostable β-galactosidase has been expressed therein.

Further, the plasmid pTG2S-112 is digested with various restriction enzymes, and the resultant fragments are inserted in suitable vectors. The resultant recombinant plasmids are introduced into *Escherichia coli* JM109, and the obtained transformants are cultured and harvested. The activity of β-galactosidase, a protein expressed in the cells, is assayed. Thus, a plasmid expressing hyperthermostable β-galactosidase can be searched for.

For example, the plasmid pTG2S-112 is digested with the restriction enzymes Eco81I (manufactured by Takara Shuzo Co., Ltd.) and Sma I. The resultant Eco81I-Sma I DNA fragment of about 2.0 kbp is purified and inserted in pUC18 to thereby obtain a recombinant plasmid.

Alternatively, with the utilization of the multicloning site of the vector (pUC18) region of pTG2S-112, ptG2S-112 is digested with the restriction enzymes Eco81I and Kpn I (manufactured by Takara Shuzo Co., Ltd.). The resultant Eco81I-Kpn I DNA fragment of about 4.7 kbp is purified, blunt-ended and self-ligated. Thus, a recombinant plasmid containing the above-mentioned Eco81I-Sma I DNA fragment of about 2.0 kbp can be obtained.

Figure 14:
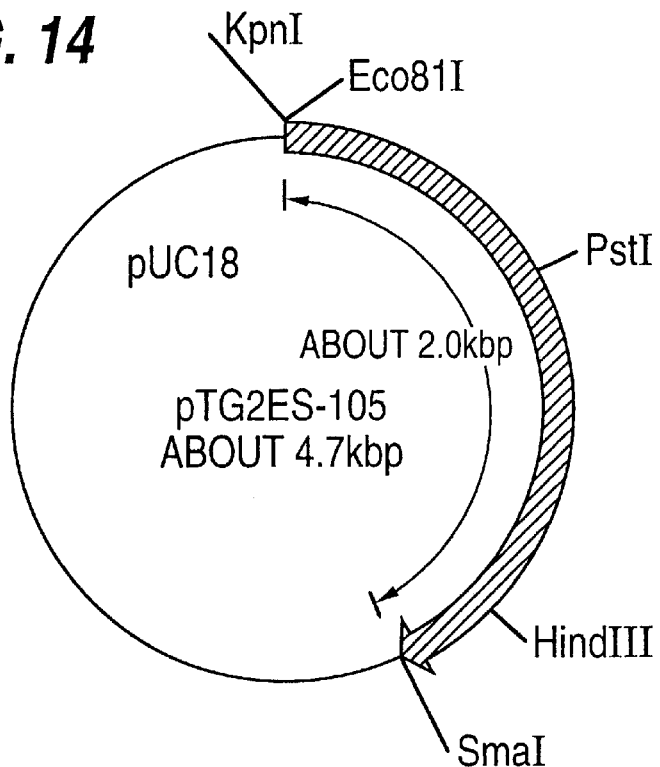
FIG. 14 shows a restriction enzyme cleavage map of the plasmid pTG2ES-105.

This plasmid is introduced into the *Escherichia coli* JM109, and the resultant colonies are assayed for the hyperthermostable β-galactosidase activities thereof. A plasmid is prepared from the colony having exhibited the activity. This plasmid is designated as plasmid pTG2ES-105. The *Escherichia coli* JM109 transformed with this plasmid is designated as *Escherichia coli* JM109/pTG2ES-105. This strain was deposited on Apr. 20, 1994 at the National Institute of Bioscience and Human-Technology Agency of Industrial Science and Technology (1–3, Higashi 1 Chome Tsukuba-shi Ibaraki-ken 305, JAPAN) under the accession number FERM BP-5023. A restriction enzyme cleavage map of the plasmid pTG2ES-105 is shown in FIG. 14, in which the thick solid line represents the fragment inserted in the plasmid pUC18.

Figure 15:
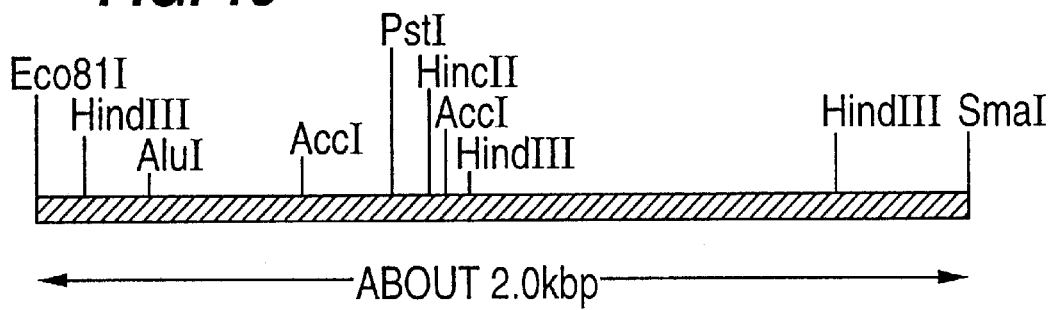
FIG. 15 shows a restriction enzyme cleavage map of one form of the hyperthermostable β-galactosidase gene of the invention.

FIG. 15 shows a restriction enzyme cleavage map of the DNA fragment derived from *Pyrococcus furiosus* and inserted in the plasmid pTG2ES-105. That is, FIG. 15 is a view showing the restriction enzyme cleavage map of the form of the hyperthermostable β-galactosidase gene obtained according to the present invention. The β-galactosidase expressed in the cells obtained by culturing the transformant designated as *Escherichia coli* JM 109/pTG2ES-105 followed by harvesting is stable irrrespective of the heat treatment conducted in the presence of 1% SDS at 100° C. for 10 minutes twice. Thus the target hyperthermostable β-galactosidase has been expressed therein.

The hyperthermostable β-galactosidase is accumulated by culturing a transformant, into which a recombinant plasmid containing the hyperthermostable β-galactosidase gene has been introduced, e.g., *Escherichia coli* JM109/pTG2S-112 or *Escherichia coli* JM109/pTG2ES-105. The purification of the hyperthermostable β-galactosidase from the culture may be effected, for example, by disrupting the harvested cells by sonication, centrifuging the lysate and subjecting the resultant supernatant to gel filtration chromatography, ion exchange chromatography, hydrophobic chromatography or the like.

When the hyperthermostable β-galactosidase is to be purified in the present invention, in particular, it is advantageous to thermally treat the cells either before or after the ultrasonication, since the contaminating proteins are denatured thereby and thus the purification can be easily carried out.

The hyperthermostable β-galactosidase obtained by expressing a gene of the present invention, for example, a gene integrated in the plasmid pTG2ES-105 has the following physicochemical properties.

(1) Activity

It has an activity of hydrolyzing lactose into galactose and glucose. Further, it has an activity of hydrolyzing o-nitrophenyl-β-D-galactopyranoside into o-nitrophenol and galactose.

Further, it has an activity of hydrolyzing o-nitrophenyl-β-D-galactopyranoside into o-nitrophenol and galactose under 50 mM phosphate buffer (pH 7.0) containing 1% SDS.

(2) Method for Determining Enzymatic Activity

[(2)-a]

In the determination of enzymatic activity, the o-nitrophenyl-β-D-galactopyranoside hydrolyzing activity of an enzyme can be determined by spectroscopically monitoring o-nitrophenol formed via the hydrolysis. Namely, 5 µl of the enzyme solution of the present invention is added to 199 µl of a 100 mM phosphate buffer solution (pH 7.0) containing 112 mM 2-mercaptoethanol, 1 mM magnesium chloride and 1% SDS. Then 1 µl of a dimethyl sulfoxide solution containing 0.4 M o-nitrophenyl-β-D-galactopyranoside is added thereto. After effecting a reaction at 95° C. for 30 minutes, the reaction is stopped by adding 100 µl of 0.1 M sodium carbonate and the absorbance of the reaction mixture at 410 nm is measured to thereby determine the amount of the o-nitrophenol thus formed. One unit of the hyperthermostable β-galactosidase obtained according to the present invention is expressed in an amount of the enzyme whereby the absorbance at 410 nm can be increased by 1.0 at 95° C. within 1 minute. The enzyme obtained in the present invention has an activity of decomposing o-nitrophenyl-β-D-galactopyranoside at pH 7.0 at 95° C. in the presence of 1% SDS.

[(2)-b]

The o-nitrophenyl-β-D-galactopyranoside hydrolyzing activity of the β-galactosidase also can be determined by the following method. The enzyme reaction was started by adding 15 µl of a dimethyl sulfoxide solution containing 1 M o-nitrophenyl-β-D-galactopyranoside into 1485 µl of McIlvaine buffer solution (pH 5.0) containing the enzyme which is in a quartz cuvette for a spectrophotometer to give a final concentration of o-nitrophenyl-β-D-galactopyranoside of 10 mM. Reaction was detected by monitoring the change of absorbance at 410 nm versus time on a spectrophotometer. Based on the change of absorbance at 410 nm per minute, o-nitrophenol released per minute was calculated by using the absorbance coefficient determined previously. One unit of enzyme activity was defined as that amount required to catalyze the release of 1 µmol o-nitrophenol per minute.

The assay of enzymatic proteins was carried out by the use of a protein assay kit (manufactured by Bio-Rad Laboratories).

(3) Thermostability

The thermostability was measured according to the following procedure in conformity with the method described in [(2)-b]. 1.5 ml of a McIlvaine buffer (pH 5.0) containing an enzyme is heated at 90° C. for a given period of time, and 1485 µl of the resultant solution is sampled therefrom. The sample is heated in a cuvette of a spectrophotometer at 90° C. for 5 minutes, and 15 µl of a dimethyl sulfoxide solution containing 1 M o-nitrophenyl-β-D-galactopyranoside is added thereto to initiate a reaction. This reaction may be traced by calculating a change in absorbance at 410 nm per minute and determining the amount of o-nitrophenol liberated per minute from a previously determined extinction coefficient of o-nitrophenol.

Figure 16:
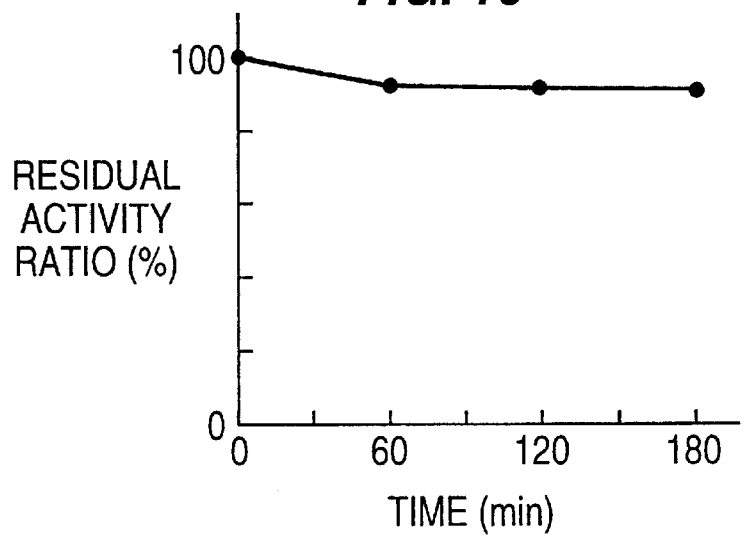
FIG. 16 shows the thermostability of an enzyme.

The enzyme of the present invention has a residual activity ratio of about 100% even after heat treatment at 90° C. for 180 minutes as shown in FIG. 16. That is, FIG. 16 shows the thermostability of the enzyme, in which the ordinate indicates the residual activity ratio (%) and the abscissa indicates the period of time (minutes) for which the enzyme is treated at 90° C.

(4) Optimum pH

The optimum pH was measured according to the method described in [(2)-b]. 2990 μl of McIlvaine buffer solution, which had a pH at an appointed value (pH 4–8) and containing 10 mM o-nitrophenyl-β-D-galactopyranoside, was incubated at 90° C. in the cuvette and the enzyme reaction was started by adding 10 μl of McIlvaine buffer solution (pH 5.0) containing the enzyme (150 units/ml) into the cuvette. Reaction was detected by monitoring the change of absorbance at 410 nm versus time on a spectrophotometer. Change of absorbance at 410 nm per minute was determined. Based on the change of absorbance at 410 nm per minute, o-nitrophenol released per minute was calculated by using the absorbance coefficient determined at each pH condition. One unit of enzyme activity was defined as that amount required to catalyze the release of 1 μmol o-nitrophenol in a minute.

Figure 17:
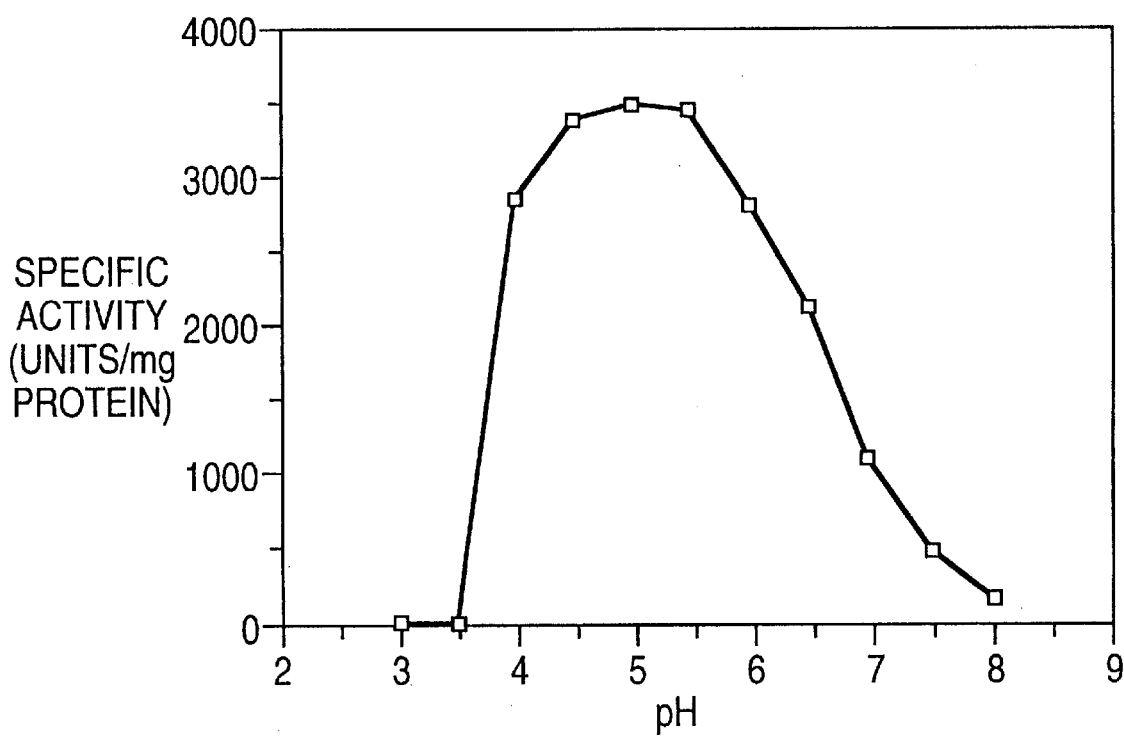
FIG. 17 shows the optimum pH of an enzyme.

As shown in FIG. 17, the enzyme of the present invention shows its maximum activity at a pH range of from 4.5 to 5.5. FIG. 17 is a graph showing the optimum pH of an enzyme wherein the ordinate represents the specific activity (units/ mg protein), while the abscissa represents treating pH.

(5) Optimum Temperature

The optimum temperature was measured according to the method described in [(2)-b]. 2990 μl of McIlvaine buffer solution (pH 5.0) containing 10 mM o-nitrophenyl-β-D-galactopyranoside was incubated at appointed temperature (45° C.–90° C.) in the cuvette and the enzyme reaction was started by adding 10 μl of the enzyme (150 units/ml). Reaction was detected by monitoring the change of absorbance at 410 nm versus time on a spectrophotometer. Change of absorbance at 410 nm per minute was determined. Based on the change of absorbance at 410 nm per minute, o-nitrophenol released per minute was calculated by using the absorbance coefficient determined at each temperature. One unit of enzyme activity was defined as that amount required to catalyze the release of 1 μmol o-nitrophenol per minute.

Figure 18:
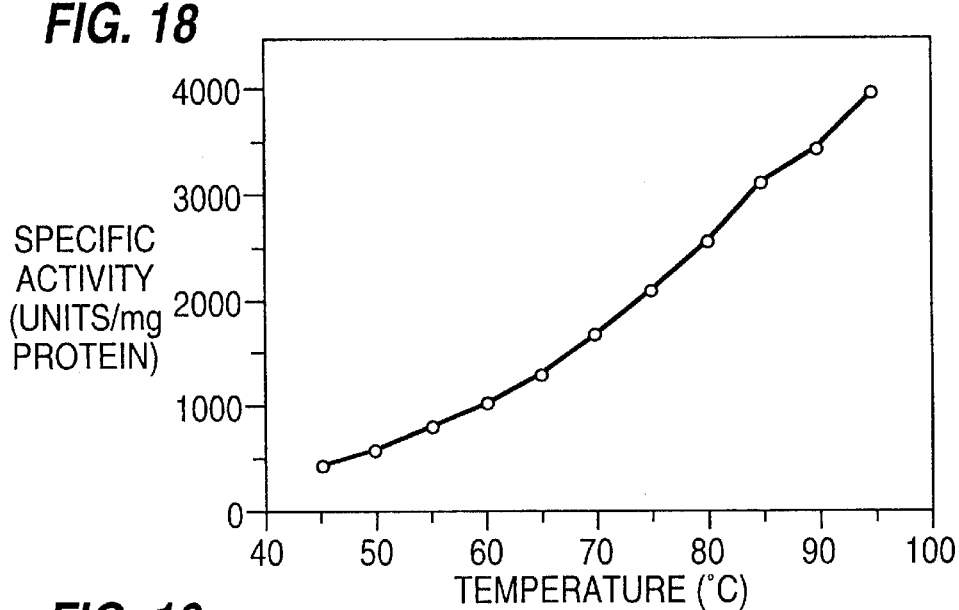
FIG. 18 shows the optimum temperature of an enzyme.

As FIG. 18 shows, the enzyme of the present invention shows its maximum activity about 95° C. FIG. 18 is a graph showing the optimum temperature of an enzyme wherein the ordinate represents the specific activity (units/mg protein), while the abscissa represents treating temperature (° C.).

(6) pH Stability

The pH stability was measured according to the method described in [(2)-b]. McIlvaine buffer solution (pH 3.0–8.0) containing 150 units/ml of the enzyme and glycine buffer solution (ph 8.0–11.0) containing 150 units/ml of the enzyme was incubated for 10 minutes at 90° C. To start the reaction, 10 μl of the enzyme solution was added to 2990 μl of McIlvaine buffer solution (pH 5.0) which contained 10 mM of o-nitrophenyl-β-D-galactopyranoside and preincubated at 90° C.

Reaction was detected by monitoring the change of absorbance at 410 nm versus time with a spectrophotometer. Change of absorbance at 410 nm in a minute was determined. Based on the change of absorbance at 410 nm per minute, o-nitrophenol released per minute was calculated by using the absorbance coefficient determined previously. One unit of enzyme activity was defined as that amount required to catalyze the release of 1 μmol o-nitrophenol in a minute.

Figure 19:
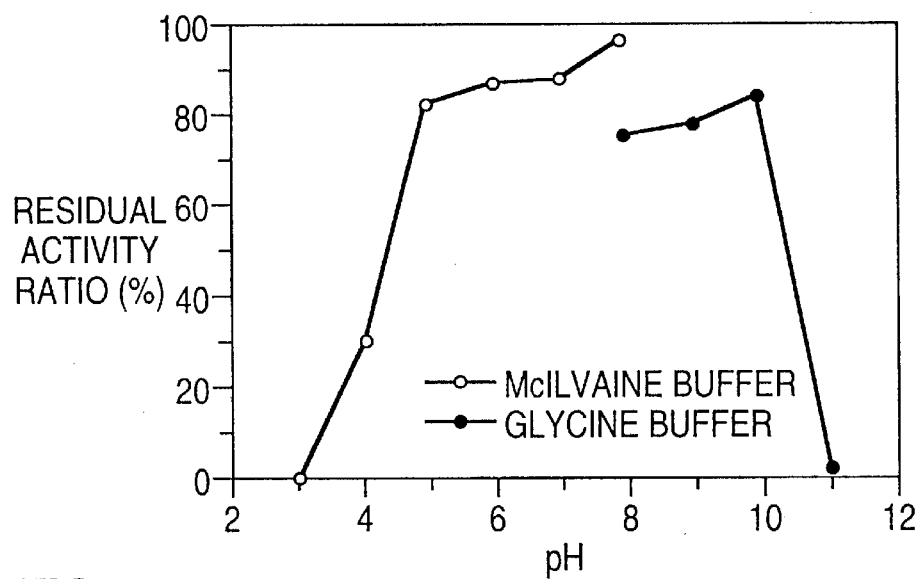
FIG. 19 shows the pH stability of an enzyme.

As FIG. 19 shows, the enzyme of the present invention sustains its activity even after treating within a pH range of from 5.0 to 10.0 at 90° C. for 10 minutes. FIG. 19 is a graph showing the pH stability of the enzyme wherein the ordinate represents the residual activity ratio (%), while the abscissa represents treating pH.

(7) Influence of Various Surfactants

The thermostability of the enzyme in the presence of each of various surfactants was measured according to the following procedure in conformity with the method described in [(2)-b]. Sodium dodecyl sulfate (SDS) (manufactured by Nacalai Tesque) was used as an anionic surfactant, hexadecyl trimethyl ammonium bromide (manufactured by Nacalai Tesque) as a cationic surfactant, polyoxyethylene (20) sorbitan monolaurate (manufactured by Wako Pure Chemical Industries, Ltd.) as a nonionic surfactant, and sodium cholate (manufactured by Nacalai Tesque) as a cholic surfactant.

In the reaction solution, the concentration of the above surfactant was adjusted to 1%. 1.5 ml of a 50 mM phosphate buffer (pH 7.0) containing an enzyme is heated at 90° C. for a given period of time, and 1485 μl of the resultant solution is sampled therefrom. The sample is heated in a cuvette of a spectrophotometer at 90° C. for 5 minutes, and 15 μl of a dimethyl sulfoxide solution containing 1 M o-nitrophenyl-β-D-galactopyranoside is added thereto to thereby initiate a reaction. This reaction may be traced by calculating a change in absorbance at 410 nm per minute and determining the amount of o-nitrophenol liberated per minute from a previously determined extinction coefficient of o-nitrophenol.

Figure 20:
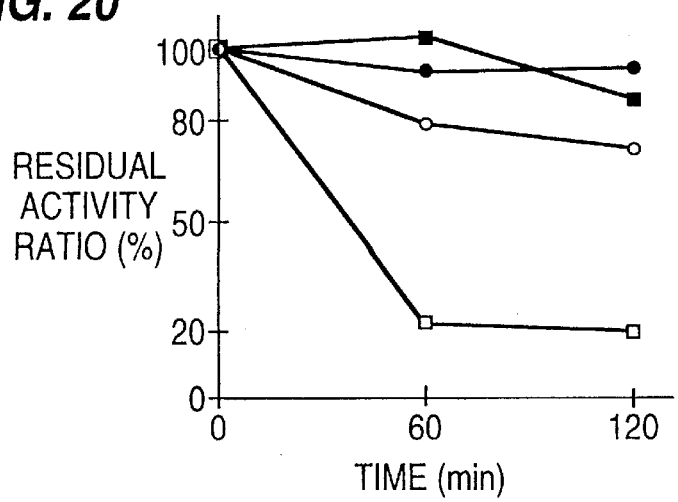
FIG. 20 shows the thermostability of an enzyme in the presence of a surfactant.

The enzyme of the present invention has a residual activity ratio of about 80% even after heat treatment at 90° C. for 120 minutes in the presence of any of the surfactants except hexadecyl trimethyl ammonium bromide, as shown in FIG. 20. In particular, the enzyme of the present invention has a residual activity ratio of about 90% even after heat treatment at 90° C. for 120 minutes in the presence of sodium dodecyl sulfate conventionally used for denaturation of proteins. FIG. 20 shows the thermostability of the enzyme in the presence of each of the various surfactants, in which the ordinate indicates the residual activity ratio (%) and the abscissa indicates the period of time (minutes) for which the enzyme is treated at 90° C.

In FIG. 20, the open square indicates hexadecyl trimethyl ammonium bromide, the solid square indicates sodium dodecyl sulfate, the open circle indicates polyoxyethylene (20) sorbitan monolaurate, and the solid circle indicates sodium cholate.

(8) Substrate Specificity

Substrate specificity is able to be determined by using p-nitrophenol-derivatives as shown in Table 5. The method is conducted as follows. 1485 μl of 150 mM sodium citrate buffer solution (pH 5.0) containing the enzyme is added to a quartz cuvette for a spectrophotometer. 15 μl of 0.1M substrate solution shown in Table 5 is added to the enzyme solution and mixed. Immediately, reaction was detected by monitoring the change of absorbance at 410 nm versus time on a spectrophotometer. As a blank test, 1485 μl of 150 mM sodium citrate buffer (pH 5.0) not containing enzyme was used, and the determination described above was performed. In the test, reaction was performed at 90° C. One unit of enzyme activity was defined as that amount required to catalyze the release of 1 μmol p-nitrophenol per minute.

According to the method described above, hydrolytic activity towards p-nitrophenyl-β-D-glucopyranoside (GlcpβNp), p-nitrophenyl-β-D-galactopyranoside (GalpβNp), p-nitrophenyl-β-D-mannopyranoside (ManpβNp), p-nitrophenyl-β-D-xylopyranoside (XylpβNp), p-nitrophenyl-β-D-fucopyranoside (FucpβNp), p-nitrophenyl-α-D-galactopyranoside (GalpαNp) (all manufactured by Nacalai Tesque), was determined.

Results are shown in Table 5. Table 5 shows the specific activity (units/mg protein) towards the above-described substrates and the relative activity (%).

TABLE 5

Specific activity of the enzyme

| Substrate | Specific activity (units/mg) | Relative activity (%) |
|---|---|---|
| GalpβNp | 192 | 100 |
| GlcpβNp | 512 | 267 |
| ManpβNp | 12.8 | 6.7 |
| XylpβNp | 51.2 | 26.7 |
| FucpβNp | 0 | 0 |
| GalpαNp | 0 | 0 |

Further, the enzymolytic activity of the enzyme was tested with the use of the following natural substrates. Specifically, each of lactose, cellobiose, methyl-β-D-glucose, salicin, arbutin, sucrose and maltose (all manufactured by Nacalai Tesque) as the substrate was dissolved in 1 ml of a 150 mM sodium citrate buffer (pH 5.0) in the final concentration of 50 mM. Each of carboxy methylcellulose (manufactured by Wako Pure Chemical Industries, Ltd.), Avicel (manufactured by Funakoshi Pharmaceutical Co., Ltd.) and laminarin (manufactured by Nacalai Tesque) was dissolved in the buffer in a final concentration of 17 g/l. Each of the above substrate solutions was heated to 90° C., and 15 μl (about 45 mU) of a phosphate (pH 7.0) of an enzyme was added thereto to effect a reaction at 90° C. for 30 minutes. The reaction was terminated by cooling with ice. The amount of glucose liberated in the reaction fluid was determined by the use of Glucose B Test Wako (manufactured by Wako Pure Chemical Industries, Ltd.).

Table 6 shows the relative activities (%) determined with respect to the other substrates when the lactose hydrolyzing activity is taken as 100%.

TABLE 6

Substrate specificity ot the enzyme

| Substrate | Relative activity (%) |
|---|---|
| Lactose | 100 |
| Cellobiose | 136 |
| methyl-β-D-glucoside | 10.2 |
| Salicin | 69.6 |
| Arbutin | 6.1 |
| Sucrose | 1.9 |
| Maltose | 1.9 |
| Carboxymethyl-cellulose | 0 |
| Avicel | 0 |
| Laminarin | 1.3 |

(9) Characteristics of Amino Acid Sequence

With respect to the amino acid sequence (SEQ ID NO. 3) encoded by the β-galactosidase gene of the plasmid pTG2ES-105, an amino acid sequence homology search was carried out by the use of NBRF-PIR of DNASIS (manufactured by Hitachi Software Engineering).

The amino acid sequences of the present enzyme and the other hyperthermostable β-galactosidase (SEQ ID NO. 3) produced by Pyrococcus furiosus were compared with those of two types of thermostable β-galactosidases (SEQ ID NO. 5 and SEQ ID NO. 6) present in Sulfolobus solfataricus, and it has for the first time become apparent that, surprisingly, some of the sequences homologous between two types of thermostable enzymes are preserved in the hyperthermostable enzyme.

FIG. 21 and FIG. 22 are views comparing the amino acid sequences shown in SEQ ID NO. 1, SEQ ID NO. 3, SEQ ID NO. 5 and SEQ ID NO. 6. The ten different sequences each designated a "box sequence" by the inventors as indicated in the FIG. 21 and FIG. 22 (Box No. 1 to Box No. 10 as shown in SEQ ID NOS: 10–19, respectively) are the above-conserved sequences (see also SEQ ID Nos. 7–9 and 20–34, directed to the upper two amino acid sequences in Box No. 1 to Box No. 10).

Other hyperthermostable β-galactosidase genes can be cloned on the basis of the above sequences, for example, by the use of a primer or probe prepared from the amino acid sequences of the Box Nos. 7, 8 and 10 respectively defined by the SEQ ID NO. 7, SEQ ID NO. 8 and SEQ ID NO. 9.

In FIG. 21 and FIG. 22, the four rows of nucleotide sequences viewed from the top to the bottom respectively correspond to SEQ ID NO. 1 (top row), SEQ ID NO. 3 (second row), SEQ ID NO. 5 (third row) and SEQ ID NO. 6 (bottom row).

As described above in detail, the present invention provides a gene coding for a hyperthermostable β-galactosidase, including an SDS-resistant β-galactosidase, and a genetic engineering process for producing the hyperthermostable β-galactosidase by using this gene. This enzyme has a high thermostability and is useful particularly in food processing at high temperature and saccharide engineering.

The present invention further provides an EcoRI fragment of about 2.2 kbp which codes for the active center of the hyperthermostable β-galactosidase. Incubation of a transformant having a recombinant plasmid containing the above fragment transduced therein gives the hyperthermostable β-galactosidase. This enzyme is not only industrially applicable but is also useful in studies on the thermostabilities of enzymes, and the like.

Furthermore, the gene isolated in accordance with the present invention, or a gene consisting of a part thereof, is useful also as a probe in screening. The use of this gene as a probe makes it easy to clone hyperthermostable β-galactosidase genes hybridizable with this gene from a number of organisms.

Genes of all the enzymes analogous to the present enzyme which have sequences slightly different from that of the present enzyme but which are expected to have a similar enzymatic activity can be obtained by effecting hybridizations using the above obtained genes as the probe under strict conditions. The term "under strict conditions" as used herein means that the probe and hybridization of a nylon membrane having a DNA immobilized thereon are performed at 65° C. for 20 hr in a solution containing 6×SSC (1×SSC being a solution obtained by dissolving 8.76 g of sodium chloride and 4.41 g of sodium citrate in 1 l of water), 1% SDS, 100 μg/ml salmon sperm DNA and 5×Denhardt's (containing each of bovine serum albumin, polyvinyl pyrrolidone and ficoll in a concentration of 0.1%).

Also, genes of all the enzymes analogous to the present enzyme which have sequences slightly different from that of the present enzyme but which are expected to have a similar enzymatic activity can be obtained by effecting gene amplification using the above obtained genes as the primer.

Moreover, screening can be performed with the use of an oligomer, as a probe, having a nucleotide sequence encoding the above amino acid sequence jointly preserved by the thermostable β-galactosidase and the hyperthermostable β-galactosidase. That is, any of the thermostable and hyperthermostable genes of the enzymes analogous to the present enzyme which are expected to have the same enzymatic activity as that of the present enzyme can be obtained from the thermophilic and hyperthermophilic bacteria, respectively, by carrying out hybridizations in the hybridization solution having the same composition as that mentioned above at a temperature 5° C. lower than the value of Tm at which each oligomer forms a complementary strand with the target DNA. Still further, screening can be performed by effecting gene amplification with the use of the above oligomer as a primer.

Whether the gene obtained by the above screening is the gene of an enzyme analogous to the present enzyme which is expected to have the same enzymatic activity as that of the present enzyme can be ascertained in the following manner. The obtained gene is ligated to an expression vector ensuring expression in a suitable host according to the conventional procedure and introduced into the host to thereby obtain a transformant. This transformant is cultured, and the β-galactosidase activity of the culture or a cell-free extract therefrom is measured by the method described herein. Thus, it can be ascertained whether this gene is the gene of an enzyme analogous to the present enzyme which is expected to have the same enzymatic activity as that of the present enzyme, i.e., which has residual activity ratio of about 90% even after treatment at 90° C. for 120 minutes in the presence of SDS.

EXAMPLES

To further illustrate the present invention in greater detail, and not by way of limitation, the following Examples will be given.

Example 1

2 l of a medium comprising 1% of trypton, 0.5% of yeast extract, 1% of soluble starch, 3.5% of Jamarin S Solid (mfd. by Jamarin Laboratory), 0.5% of Jamarin S Liquid (mfd. by Jamarin Laboratory), 0.003% of $MgSO_4$, 0.001% of Nacl, 0.0001% of $FeSO_4 \cdot 7H_2O$, 0.0001% of $CoSO_4$, 0.0001% of $CaCl_2 \cdot 7H_2O$, 0.0001% of $ZnSO_4$, 0.1 ppm of $CuSO_4 \cdot 5H_2O$, 0.1 ppm of $KAl(SO_4)_2$, 0.1 ppm of $H_3BO_3$, 0.1 ppm of $Na_2MoO_4 \cdot 2H_2O$ and 0.25 ppm of $NiCl_2 \cdot 6H_2O$ was fed into a 2 l medium bottle and sterilized at 120° C. for 20 minutes. After eliminating the dissolved oxygen by blowing nitrogen gas, the medium was inoculated with the above-mentioned strain, which was then stationarily cultivated at 95° C. for 16 hours.

After completion of the cultivation, cells were collected by centrifuging. Then these cells were suspended in 30 ml of a 50 mM phosphate buffer solution (pH 7.0) containing 1 mM of EDTA, 1 mM of PMSF and 0.1% of Triton X-100 and disrupted by ultrasonication. This suspension of the disrupted cells was centrifuged at 4° C. at 12,000 rpm for 10 minutes and the supernatant was separated for use as a crude enzyme solution. When the content of the enzyme in this crude enzyme solution was measured, it was found out that 169.2 U of β-galactosidase was obtained.

The crude enzyme solution thus obtained was adsorbed by a DEAE Toyopearl M650 column (mfd. by Tosoh Corporation) which had previously been equilibrated with a 50 mM phosphate buffer solution (pH 7.0) containing 1 mM of EDTA. After washing this column with the above-mentioned buffer solution and developing with the same buffer solution by linear gradient elution with 0 to 0.5 M sodium chloride, two types of active fractions were eluted. These active fractions were named E-I and E-II fractions in order of elution. The active fractions were separately combined.

To the E-I fraction was added 3.6 M ammonium sulfate in such a manner as to give a concentration of 1.2 M. Then the obtained mixture was adsorbed by an HIC-Cartridge Column (mfd. by Bio-Rad) which had been previously equilibrated with a 50 mM phosphate buffer solution (pH 7.0) containing 1.2 M of ammonium sulfate and 1 mM of EDTA. After washing this column with a 50 mM phosphate buffer solution (pH 7.0) containing 1.2 M of ammonium sulfate and 1 mM of EDTA and developing with a 50 mM phosphate buffer solution (pH 7.0) containing 1 mM of EDTA by linear gradient elution with 1.2 to 0 M ammonium sulfate, active fractions were eluted. These active fractions were combined together, concentrated with Centriflo® CF25 (mfd. by Amicon) and MOLCUT II GC (mfd. by Millipore Corp.) and subjected to gel filtration by using a Superose 12 Column (mfd. by Pharmacia; 10×300 mm) which had been previously equilibrated with 50 mM phosphate buffer solution (pH 7.2) containing 100 mM of sodium chloride. Thus two active fractions were obtained and named E-I-1 and E-I-2 in order of elution. When the contents of enzymes in the fractions E-I-1 and E-I-2 were measured, it was found that 1.8 U of E-I-1 and 6.9 U of E-I-2 were obtained.

To the E-II fraction was added 3.6 M ammonium sulfate in such a manner as to give a concentration of 1.2 M. Then the obtained mixture was adsorbed by an HIC-Cartridge Column (mfd. by Bio-Rad) which had been previously equilibrated with a 50 mM phosphate buffer solution (pH 7.0) containing 1.2 M of ammonium sulfate and 1 mM of EDTA. After eluting this column with a 50 mM phosphate buffer solution (pH 7.0) containing 1.2 M of ammonium sulfate and 1 mM of EDTA, active fractions were eluted. These active fractions were combined together, concentrated with MOLCUT II GC (mfd. by Millipore Corp.) and subjected to gel filtration by using a Superose 12 Column (mfd. by Pharmacia: 10×300 mm) which had been previously equilibrated with a 50 mM phosphate buffer solution (pH 7.2) containing 100 mM of sodium chloride. When the content of the enzyme in the fraction E-II was measured, it was found that 3.4 U of the enzyme was obtained.

The active fractions were detected by measuring the activity of hydrolyzing o-nitrophenyl-β-D-galactopyranoside.

Example 2

By using the enzyme solutions as obtained in Example 1 above, effects of sodium dodecyl sulfate (SDS) on the enzymatic activities thereof were examined. As a buffer solution, McIlvaine's buffer solution of pH 6.0 was used for E-I-1 while McIlvaine's buffer solution of pH 6.6 was used for E-I-2 and E-II. 9.13 mU of E-I-1, 17.25 mU of E-I-2 and 11.35 mU of E-II were employed. To each enzyme was added the above-mentioned buffer solution containing 112 mM of 2-mercaptoethanol and 1 mM of magnesium chloride in such a manner as to give a total volume of 189 μl. After adding 10 μl of a 10% sodium dodecyl sulfate solution, 1 μl of a 0.4 M o-nitrophenyl-D-galactopyranoside solution was further added thereto to effect a reaction at 90° C. for 30 minutes. Then the reaction was stopped by adding 100 μl of a 0.1 M sodium carbonate solution. The amount of the o-nitrophenol thus formed was measured by monitoring the absorbance at 410 nm. As shown in Table 7, E-II, among the enzymes of the present invention, sustained its activity.

TABLE 7

Influence of sodium dodecyl sulfate on the activities of β-galactosidases

| Enzymes | Residual Activities (%) | |
|---|---|---|
|  | SDS(+) | SDS(−) |
| E-I-1 | 0 | 100 |
| E-I-2 | 6.9 | 100 |
| E-II | 126.2 | 100 |

Example 3

(1) Preparation of *Pyrococcus furiosus* Genome DNA

*Pyrococcus furiosus* DSM 3638 was incubated in the following manner. 2 l of a medium comprising 1% of trypton, 0.5% of yeast extract, 1% of soluble starch, 3.5% of Jamarin S Solid (mfd. by Jamarin Laboratory), 0.5% of Jamarin S Liquid (mfd. by Jamarin Laboratory), 0.003% of $MgSO_4$, 0.001% of NaCl, 0.0001% of $FeSO_4 \cdot 7H_2O$, 0.0001% of $CoSO_4$, 0.0001% of $CaCl_2 \cdot 7H_2O$, 0.0001% of $ZnSO_4$, 0.1 ppm of $CuSO_4 \cdot 5H_2O$, 0.1 ppm of $KAl(SO_4)_2$, 0.1 ppm of $H_3BO_3$, 0.1 ppm of $Na_2MoO_4 \cdot 2H_2O$ and 0.25 ppm of $NiCl_2 \cdot 6H_2O$ was fed into a 2 l medium bottle and sterilized at 120° C. for 20 minutes. After eliminating the dissolved oxygen by blowing nitrogen gas, the medium was inoculated with the above-mentioned strain, which was then stationarily incubated at 95° C. for 16 hours. After the completion of the incubation, cells were collected by centrifuging.

Then the collected cells were suspended in 4 ml of a 0.05 M Tris-HCl (pH 8.0) containing 25% of sucrose. To the obtained suspension were added 0.8 ml of lysozyme [5 mg/ml, 0.25 M Tris-HCl (pH 8.0)] and 2 ml of 0.2 M EDTA. After maintaining at 20° C. for 1 hour, 24 ml of an SET solution [150 mM Nacl, 1 mM EDTA, 20 mM Tris-HCl (pH 8.0)] was added. Further, 4 ml of 5% SDS and 400 μl of proteinase K (10 mg/ml) were added thereto, followed by a reaction at 37° C. for 1 hour. After the completion of the reaction, the reaction mixture was extracted with chloroform/phenol and precipitated from ethanol. Thus approximately 3.2 mg of a genome DNA was prepared.

(2) Preparation of Cosmid Protein Library

400 μg of the *Pyrococcus furiosus* DSM 3638 genome DNA was partially digested with Sau 3AI in a buffer solution for Sau 3AI [50 mM Tris-HCl (pH 7.5), 10 mM $MgCl_2$, 1 mM dithio-threitol, 100 mM Nacl] and fractionated according to the size by density gradient centrifugation. One μg of Triple Helix Cosmid Vector was cleaved with Bam HI and mixed with 140 μg of the genome DNA fragments of 35 to 50 kbp which had been obtained by the fractionation as described above. After ligating with the use of a Ligation Kit (mfd. by Takara Shuzo Co., Ltd.), the Pyrococcus genome DNA fragments were packaged into λ-phage particles by the in vitro packaging method using Gigapack II Gold (mfd. by Stratagene). By using a part of the phage solution thus obtained, *E. coli* DH5αMCR was transformed to thereby give a cosmid library.

From several colonies thus obtained, cosmid DNAs were prepared and it was confirmed that they had an inserted fragment of an appropriate size in common. Next, 500 colonies were suspended in 2 ml of an L-broth medium containing 0.01% of ampicillin and incubated under shaking at 37° C. for 16 hours. The culture was centrifuged and cells were collected as a precipitate. These cells were suspended in 20 mM Tris-HCl (pH 8.0) and thermally treated at 100° C. for 10 minutes. Subsequently, they were ultrasonicated and further thermally treated at 100° C. for 10 minutes. After centrifuging, the supernatant was collected and referred to as a crude enzyme solution. Thus 500 cosmid protein libraries were prepared.

(3) Selection of cosmid containing β-galactosidase gene

The cosmid protein libraries obtaining in the above Example 3-(2) were divided into 50 groups each having 10 cosmid protein libraries. Then the β-galactosidase activity of the crude enzyme solution of each protein library group was determined. Namely, 10 μl of the crude enzyme solution was added to 99.5 μl of a 100 mM phosphate buffer solution (pH 7.3) containing 112 mM of 2-mercaptoethanol and 1 mM of magnesium chloride. After adding 0.5 μl of a dimethyl sulfoxide solution containing 0.4 M of o-nitrophenyl-β-D-galactopyranoside, the mixture was reacted at 95° C. for 30 minutes. Then the reaction was stopped by adding 50 μl of 0.1 M sodium carbonate and the absorbance at 410 nm was measured. Thus the amount of the formed o-nitrophenol was determined.

Next, β-galactosidase activities of 60 protein libraries constituting six groups of the cosmid protein libraries showing β-galactosidase activity were further measured. Thus seven cosmid proteins having β-galactosidase activity were specified and seven could DNAs corresponding thereto were specified.

(4) Preparation of plasmid pTGE-101 and production of thermostable β-galactosidase Seven cosmid DNAs obtained in the above Example 3-(3) were completely digested with a restriction enzyme EcoRI and electrophoresed on a gel. Thus an EcoRI DNA fragment of about 2.2 kbp which was common to these seven cosmid DNAs was purified. Then a vector pUC19 was cleaved at the EcoRI site and dephosphorylated at the end. Then the above-mentioned EcoRI DNA fragment of about 2.2 kbp was ligated onto this plasmid with the use of a ligation kit. By using the reaction mixture thus obtained, *E. coli* JM109 was transformed. Then a DNA was extracted from the transformant, cleaved with EcoRI and electrophoresed on an agarose gel. Thus the presence of the EcoRI fragment of about 2.2 kpb inserted thereinto was confirmed. The obtained plasmid and the transformant were named respectively pTGE-101 and *Escherichia coli* JM109/pTGE-101.

This EcoRI DNA fragment of about 2.2 kpb was cleaved with several restriction enzymes and analyzed by agarose gel electrophoresis. FIG. 6 shows a restriction enzyme map of the obtained plasmid pTGE-101 having the EcoRI DNA fragment of about 2.2 kbp.

*Escherichia coli* JM109/pTGE-101 was suspended in 5 ml of an L-broth medium containing 0.01% of ampicillin and incubated under shaking at 37° C. for 16 hours. The culture was centrifuged and the cells thus collected were suspended in a 50 mM phosphate buffer solution (pH 7.0) containing 1 mM of EDTA and thermally treated at 100° C. for 10 minutes. Then the cells were ultrasonicated and further treated at 100° C. for 10 minutes. After centrifuging, the supernatant was separated for use as a crude enzyme solution. Then the β-galactosidase activity was determined in accordance with the method as described in the above Example 3-(3) except that 5 μl of this crude enzyme solution was used. As a result, this crude enzyme solution showed no activity. Then another crude enzyme solution was prepared in the same manner as the one described above except that the thermal treatments (100° C., 10 minutes, twice) were omitted. Then the β-galactosidase activity of the crude enzyme solution was determined in accordance with the method of Example 3-(3) except that the reaction temperature was adjusted to 70° C. This crude enzyme solution had an activity of decomposing o-nitrophenyl-β-D-galactopyranoside at pH 7.3 at 70° C. Namely, a gene coding for a thermostable β-galactosidase showing an activity at 70° C. had been inserted into pTGE-101.

(5) Preparation of plasmid pTGH-301

The EcoRI DNA fragment (about 2.2 kbp) obtained in the above Example 3-(4) was labeled with ($\alpha$-$^{32}$P) dCTP (3000 Ci/mmol; mfd. by Amersham) by using a Random Primer Labeling Kit (mfd. by Takara Shuzo Co., Ltd.). By using the labeled DNA fragment thus obtained as a probe, the cosmid DNAs as specified in the above Example 3-(3), which had been completely digested with Hind III and separated by electrophoresis, were analyzed by Southern hybridization. Thus a Hind III DNA fragment of about 3.5 kbp hybridized by the above probe was identified and purified. Next, pUC19 was cleaved at the Hind III site and dephosphorylated at the end. The above-mentioned Hind III DNA fragment was ligated onto this plasmid by using a ligation kit and *E. coli* JM109 was transformed thereby. The obtained plasmid was named plasmid pTGH-301, while the transformant was named *Escherichia coli* JM109/pTGH-301.

*Escherichia coli* JM109/pTGH-301 was suspended in 5 ml of an L-broth medium containing 0.01% of ampicillin and incubated under shaking at 37° C. for 16 hours. The culture was centrifuged and the cells thus collected were suspended in a 50 mM phosphate buffer solution (pH 7.0) containing 1 mM of EDTA and thermally treated at 100° C. for 10 minutes. Subsequently, the cells were ultrasonicated and then thermally treated again at 100° C. for 10 minutes. After centrifuging, the supernatant was separated for use as a crude enzyme solution. The β-galactosidase activity was determined in accordance with the method of the above Example 3-(3) except that 5 μl of this crude enzyme solution was used. As a result, the activity of a hyperthermostable β-galactosidase which can withstand the thermal treatment at 100° C. for 20 minutes was observed in the crude enzyme solution.

The above-mentioned Hind III DNA fragment of about 3.5 kbp was cleaved with several restriction enzymes and analyzed by agarose gel electrophoresis. FIG. 7 shows a restriction enzyme map of the plasmid pTGH-301 containing the Hind III DNA fragment (about 3.5 kpb) obtained above. *E. coli* JM109 transformed by the plasmid pTGH-301 containing the hyperthermostable β-galactosidase gene was expressed as *Escherichia coli* JM109/pTGH-301 and has been deposited with Fermentation Research Institute of the Agency of Industrial Science and Technology under the accession number FERM P-13348.

(6) Preparation of plasmid pTCEH-401

The above-mentioned plasmid pTGH-301 was digested with EcoRI and electrophoresed on an agarose gel. Among DNA fragments of about 3.0 kbp, about 2.2 kbp and about 1.0 kbp thus separated, two DNA fragments (of about 3.0 kbp and about 2.2 kbp) were recovered. The DNA fragment of about 3.0 kbp was dephosphorylated with the use of alkaline phosphatase (mfd. by Takara Shuzo Co., Ltd.) and ligated by mixing with the DNA fragment of about 2.2 kbp, followed by transduction into *E. coli* JM109. The hyperthermostable β-galactosidase activities of the colonies thus formed were determined. From colonies showing the activity, a plasmid was prepared and named pTGEH-401. *E. coli* JM109 containing this plasmid was named *Escherichia coli* JM109/pTGEH-401, and deposited at the National Institute of Bioscience and Human-Technology Agency of Industrial Science and Technology, Japan, under the accession number of FERM BP-4468.

FIG. 8 shows a restriction enzyme map of the plasmid pTGEH-401. FIG. 9 shows a restriction enzyme map of the hyperthermostable β-galactosidase gene of about 2.5 kbp, which originates in *Pyrococcus furiosus* and is obtained in accordance with the present invention, inserted into the plasmid pTGEH-401.

Example 4

Determination of DNA sequence of the hyperthermostable β-galactosidase gene

The DNA fragment of about 3.5 kbp containing the hyperthermostable β-galactosidase gene inserted in the plasmid pTGH-301 was cleaved with several restriction enzymes and subcloned into plasmid vector pUC118. The DNA sequences of each fragment subcloned were determined by the dideoxy method using BcaBest™ Dideoxy Sequencing Kit (mfd. by Takara Shuzo, Co., LTD.). SEQ ID NO. 2 in the Sequence Listing shows the DNA sequence of the DNA fragment containing the hyperthermostable β-galactosidase gene which has been inserted in the plasmid pTGH-301. SEQ ID NO. 1 in the Sequence Listing shows the amino acid sequence of the hyperthermostable β-galactosidase which is deduced from the DNA sequence shown in SEQ ID NO. 2.

Example 5

Production of hyperthermostable β-galactosidase

*Escherichia coli* JM109/pTGH-301 (FERM P-13348) having the plasmid pTGH-301 containing the hyperthermostable β-galactosidase gene of the present invention transduced therein, which was obtained in the above Example 3, was suspended in 5 ml of an L-broth medium containing 0.01% of ampicillin and incubated under shaking at 37° C. for 16 hours. Then the culture was suspended in 1.2 l of a medium of the same conditions and incubated under shaking at 37° C. for 16 hours. After centrifuging the culture, the cells thus collected were suspended in a 50 mM phosphate buffer solution (pH 7.0) containing 1 mM of EDTA and thermally treated at 100° C. for 10 minutes.

Next, the cells were ultrasonicated and thermally treated again at 100° C. for 10 minutes. After centrifuging, the supernatant was separated for use as a crude enzyme solution. This crude enzyme solution had 20 U of o-nitrophenyl-β-D-galactopyranoside-decomposing activity per ml of the L-broth medium at pH 7.3 at 95° C. This crude enzyme solution was concentrated with MOLCUT II (cutoff molecular weight: 10,000, mfd. by Millipore Corp.) and gel-filtered through a Superose 12 Column (10×300 mm; mfd. by Pharmacia), which had been equilibrated with a 50 mM phosphate buffer solution (pH 7.2) containing 100 mM of NaCl, and an active fraction was collected. The active fraction was concentrated with MOLCUT II (cutoff molecular weight: 10,000; mfd. by Millipore Corp.) and adsorbed by 1 ml of an APTG affinity column (mfd. by MoBi Tec), which had been equilibrated with a 20 mM glycine sodium buffer solution (pH 7.5) containing 10 mM of MgCl$_2$, and 200 mM of NaCl. After maintaining at room temperature for 1 hour, the column was washed with 12.5 ml of a 20 mM glycine sodium buffer solution (pH 7.5) containing 10 mM of MgCl$_2$, and 200 mM of NaCl and then eluted with a 100 mM glycine sodium buffer solution (pH 10.0). An active fraction was separated and thus a purified enzyme preparation was obtained. When electrophoresed on a 7.5% SDS-polyacrylamide gel, this preparation showed a single band.

Similarly, *Escherichia coli* JM109/pTGEH-401 having the plasmid pTGEH-401 containing the hyperthermostable β-galactosidase gene of the present invention transduced therein was incubated in the same manner as the one described above. From the culture, an active fraction of the hyperthermostable β-galactosidase was purified and thus a hyperthermostable β-galactosidase preparation was obtained.

Example 6

(1) Preparation of *Pyrococcus furiosus* genome DNA

*Pyrococcus furiosus* DSM 3638 was incubated in the following manner. 2 l of a medium comprising 1% trypton, 0.5% yeast extract, 1% soluble starch, 3.5% Jamarin S Solid (manufactured by Jamarin Laboratory), 0.5% Jamarin S Liquid (manufactured by Jamarin Laboratory), 0.003% $MgSO_4$, 0.001% NaCl, 0.0001% $FeSO_4 \cdot 7H_2O$, 0.0001% $CoCO_4$, 0.0001% $CaCl_2 \cdot 7H_2O$, 0.0001% $ZnSO_4$, 0.1 ppm $CuSO_4 \cdot 5H_2O$, 0.1 ppm $KAl(SO_4)_2$, 0.1 ppm $H_3BO_3$, 0.1 ppm $Na_2MoO_4 \cdot 2H_2O$ and 0.25 ppm $NiCl_2 \cdot 6H_2O$ was fed into a 2 l medium bottle and sterilized at 120° C. for 20 minutes. After eliminating the dissolved oxygen by blowing nitrogen gas, the medium was inoculated with the above-mentioned strain, which was then stationarily incubated at 95° C. for 16 hours. After the completion of the incubation, cells were collected by centrifuging.

Then the collected cells were suspended in 4 ml of a 0.05 M Tris-HCl (pH 8.0) containing 25% sucrose. To the obtained suspension were added 0.8 ml of lysozyme [5 mg/ml, 0.25 M Tris-HCl (pH 8.0)] and 2 ml of 0.2 M EDTA. After maintaining at 20° C. for 1 hour, 24 ml of an SET solution [150 mM NaCl, 1 mM EDTA, 20 mM Tris-HCl (pH 8.0)] was added. Further, 4 ml of 5% SDS and 400 µl of proteinase K (10 mg/ml) were added thereto, followed by reaction at 37° C. for 1 hour. After the completion of the reaction, the reaction mixture was extracted with chloroform/phenol and precipitated from ethanol. Thus approximately 3.2 mg of genome DNA was prepared.

(2) Preparation of cosmid protein library

400 µg of the *Pyrococcus furiosus* DSM 3638 genome DNA was partially digested with Sau 3AI in a buffer solution for Sau 3AI [50 mM Tris-HCl (pH 7.5), 10 mM $MgCl_2$, 1 mM dithiothreitol, 100 mM NaCl] and fractionated according to size by density gradient centrifugation. 1 µg of Triple Helix Cosmid Vector was cleaved with Bam HI and mixed with 140 µg of the genome DNA fragments of 35 to 50 kbp which had been obtained by the fractionation as described above. After ligating with the use of a Ligation Kit (manufactured by Takara Shuzo Co., Ltd.), the Pyrococcus genome DNA fragments were packaged into λ-phage particles by the in vitro packaging method using Gigapack II Gold (manufactured by Strategene). By using a part of the phage solution thus obtained, *Escherichia coli* DH5αMCR was transformed to thereby give a cosmid library.

From several colonies thus obtained, cosmid DNAs were prepared and it was confirmed that they had an inserted fragment of an appropriate size in common. Next, 500 colonies were suspended in 2 ml of an L-broth medium containing 0.01% of ampicillin and incubated with shaking at 37° C. for 16 hours. The culture was centrifuged and cells were collected as a precipitate. These cells were suspended in 20 mM Tris-HCl (pH 8.0) and thermally treated at 100° C. for 10 minutes. Subsequently, they were ultrasonicated and further thermally treated at 100° C. for 10 minutes. After centrifuging, the supernatant was collected and referred to as a crude enzyme solution. Thus 500 cosmid protein libraries were prepared.

(3) Selection of cosmid containing β-galactosidase gene

The β-galactosidase activity of the crude enzymatic solution of the 500 cosmid protein library obtained in Example 6-(2) was determined. Specifically, 10 µl of the crude enzymatic solution was added to 99.5 µl of a 100 mM phosphate buffer (pH 7.0) containing 112 mM 2-mercaptoethanol, 1 mM magnesium chloride and 1% SDS. Subsequently, 0.5 µl of a dimethyl sulfoxide solution containing 0.4 M o-nitrophenyl-β-D-galactopyranoside was added and reacted at 95° C. for 30 minutes. This reaction was terminated by adding 50 µl of 0.1 M sodium carbonate. The absorbance at 410 nm was measured, thereby determining the amount of the formed o-nitrophenol.

One cosmid protein with β-galactosidase activity was selected from the 500 cosmid protein library, and one cosmid DNA corresponding thereto was identified.

(4) Preparation of plasmid pTG2S-112 and production of thermostable β-galactosidase The single cosmid DNA obtained in Example 6-(3) was completely digested with the restriction enzyme Sma I. Separately, pUC18 as a vector was cleaved at its Sma I site, followed by end dephosphorylation. The above Sma I digested DNA fragment was ligated to the vector plasmid by the use of a ligation kit. The *Escherichia coli* JM109 was transformed with the use of the resultant reaction solution. The transformant was suspended in 5 ml of an L-broth medium containing 0.01% ampicillin and cultured while shaking at 37° C. for 16 hr. The resultant culture was centrifuged, and the recovered cells were suspended in a 50 mM phosphate buffer (pH 7.0) containing 1 mM EDTA. The suspension was heated at 100° C. for 10 minutes, sonicated, further heated at 100° C. for 10 minutes, and centrifuged to thereby obtain a supernatant as a crude enzymatic solution. The β-galactosidase activity was assayed by the same activity assay method as that of Example 6-(3) except that 5 µl of this crude enzymatic solution was used. The hyperthermostable β-galactosidase activity exhibiting resistance to heat treatment at 100° C. for 20 minutes was recognized in the crude enzymatic solution.

The plasmid corresponding to this crude enzymatic solution was designated plasmid pTG2S-112. The plasmid pTG2S-112 was introduced into the *Escherichia coli* JM109, thereby obtaining a transformant. This transformant was designated as *Escherichia coli* JM109/pTG2S-112.

(5) Preparation of plasmid pTG2ES-105

The plasmid pTG2S-112 containing the Sma I DNA fragment of about 4 kbp obtained in Example 6-(4) was completely digested with the restriction enzymes Eco81I and Kpn I. The resultant Eco81I-Kpn I DNA fragment of about 4.7 kbp was purified, blunt-ended and self-ligated.

The obtained plasmid was designated plasmid pTG2ES-105. This plasmid was introduced into the *Escherichia coli* JM109, thereby obtaining a transformant. This transformant was designated as *Escherichia coli* JM109/pTG2ES-105. This strain was deposited on Apr. 20, 1994 at the National Institute of Bioscience and Human-Technology Agency of Industrial Science and Technology (1-3, Higashi 1 Chome Tsukuba-shi Ibaraki-ken 305, JAPAN) under the accession number FERM BP-5023.

FIG. 14 shows a restriction enzyme cleavage map of the plasmid pTG2ES-105, and FIG. 15 shows a restriction enzyme cleavage map of the hyperthermostable β-galactosidase gene of about 2.0 kbp obtained according to the present invention which was derived from *Pyrococcus furiosus* and inserted in the plasmid pTG2ES-105.

Example 7

Determination of nucleotide sequence of hyperthermostable β-galactosidase gene

Deletion mutants were prepared from the above fragment of about 2.0 kbp including the hyperthermostable β-galactosidase gene inserted in the plasmid pTG2ES-105 with the use of Deletion Kit for Kilo Sequence (manufactured by Takara Shuzo Co., Ltd.), and the nucleotide sequences of the resultant fragments were determined.

The determination of the nucleotide sequences was conducted by the dideoxy method in which use was made of the Bca Bast Dideoxy Sequencing Kit (manufactured by Takara Shuzo Co., Ltd.).

SEQ ID NO. 4 shows the nucleotide sequence of the DNA fragment including the hyperthermostable β-galactosidase gene inserted in the plasmid pTG2ES-105. SEQ ID NO. 3 shows the amino acid sequence of the hyperthermostable β-galactosidase encoded by the above nucleotide sequence.

Example 8

(1) Production of hyperthermostable β-galactosidase

The *Escherichia coli* JM109/pTG2ES-105 (FERM BP-5023) obtained in Example 6, into which the plasmid pTG2ES-105 containing the hyperthermostable β-galactosidase gene of the present invention had been introduced, was suspended in 5 ml of an L-broth medium containing 0.01% ampicillin and cultured while shaking at 37° C. for 16 hr. The culture was suspended in 1.2 l of the medium of the same composition and cultured while shaking at 37° C. for 16 hr. The resultant culture was centrifuged, and the recovered cells were suspended in a 50 mM phosphate buffer (pH 7.0) containing 1 mM EDTA. The suspension was heated at 100° C. for 10 minutes, sonicated, further heated at 100° C. for 10 minutes, and centrifuged to thereby obtain a supernatant as a crude enzymatic solution.

The specific activity of β-galactosidase in the crude enzymatic solution was about 740 units/mg at pH 5.0 and 90° C.

EFFECTS OF THE INVENTION

The present invention provides hyperthermostable β-galactosidases and further provides a β-galactosidase having a hyperthermostability that can exert its action even in the presence of sodium dodecyl sulfate which is a powerful surfactant. The use of the hyperthermostable β-galactosidase gene of the present invention makes it possible to industrially produce a hyperthermostable β-galactosidase. By using the hyperthermostable β-galactosidase gene of the present invention or part thereof as a probe, hyperthermostable β-galactosidase genes originating in various organisms can be obtained.

---

What we claim is:

1. An isolated DNA encoding a polypeptide possessing β-galactosidase activity of about 80% or above after being subjected to heat treatment at 90° C. for 120 minutes, and having a DNA sequence which hybridizes with a DNA sequence complementary to the DNA sequence shown in SEQ ID NO. 2 under stringent conditions.

2. An isolated DNA encoding a polypeptide possessing SDS-resistant β-galactosidase activity of about 80% or above after being subjected to heat treatment at 90° C. for 120 minutes in the presence of 1% SDS, and having a DNA sequence which hybridizes with a DNA sequence complementary to the DNA sequence shown in SEQ ID NO. 4 under stringent conditions.

3. A method of cloning a DNA having a sequence encoding a polypeptide possessing SDS-resistant β-galactosidase activity of about 80% or above after being subjected to heat treatment at 90° C. for 120 minutes in the presence of 1% SDS, which comprises:

isolating a gene which hybridizes under stringent conditions with a probe, said probe selected from the group consisting of:
   (a) a DNA having the DNA sequences shown in SEQ ID No. 4,
   (b) a DNA encoding the amino acid sequence shown in SEQ ID No. 3,
   (c) a DNA fragment of SEQ ID NO. 2 or 4, which encodes the amino acid sequence shown in SEQ ID No. 10, 11, 12, 13, 14, 15, 16, 17, 18 or 19, and
   (d) a DNA produced by PCR amplification of a gene library of a hyperthermophilic bacteria using PCR primers selected from the group consisting of DNA fragments encoding the amino acid sequence shown in SEQ ID No. 7, 8, 9, 2, 21, 22, 23, 24, 25, 26, 27, 28, 29, 30, 31, 32, 33 or 34, ligating said gene to an expression vector and introducing said vector into a host cell, and measuring the β-galactosidase activity of said transformed host cell.

4. The method of cloning a DNA according to claim 3, wherein the probe is the DNA having the DNA sequence shown in SEQ ID No. 4.

5. The method of cloning a DNA according to claim 3, wherein the probe is the DNA encoding the amino acid sequence shown in SEQ ID No. 3.

6. The method of cloning a DNA according to claim 3, wherein the probe is the DNA fragment of SEQ ID NO. 2 or 4, which encodes the amino acid sequence shown in SEQ ID No. 10, 11, 12, 13, 14, 15, 16, 17, 18 or 19.

7. The method of cloning a DNA according to claim 3, wherein the probe is the DNA produced by PCR amplification of a gene library of a hyperthermophilic bacteria using PCR primers selected from the group consisting of DNA fragments encoding the amino acid sequence shown in SEQ ID No. 7, 8, 9, 20, 21, 22, 23, 24, 25, 26, 27, 28, 29, 30, 31, 32, 33 or 34.

* * * * *

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
      (A) LENGTH: 510 amino acid residues
      (B) TYPE: amino acid
      (C) STRANDEDNESS: single
      (D) TOPOLOGY: linear (ii) MOLECULE TYPE: peptide (vi) ORIGINAL SOURCE:
      (A) ORGANISM: Pyrococcus furiosus (xi) SEQUENCE DESCRIPTION: SEQ ID NO:1:

```
Met Phe Pro Glu Lys Phe Leu Trp Gly Val Ala Gln Ser Gly Phe
 1               5                  10                  15

Gln Phe Glu Met Gly Asp Lys Leu Arg Asn Ile Asp Thr Asn
                20                  25                  30

Thr Asp Trp Trp His Trp Val Arg Asp Lys Thr Asn Ile Glu Lys
                35                  40                  45

Gly Leu Val Ser Gly Asp Leu Pro Glu Glu Gly Ile Asn Asn Tyr
                50                  55                  60

Glu Leu Tyr Glu Lys Asp His Glu Ile Ala Arg Lys Leu Gly Leu
                65                  70                  75

Asn Ala Tyr Arg Ile Gly Ile Glu Trp Ser Arg Ile Phe Pro Trp
                80                  85                  90

Pro Thr Thr Phe Ile Asp Val Asp Tyr Ser Tyr Asn Glu Ser Tyr
                95                  100                 105

Asn Leu Ile Glu Asp Val Lys Ile Thr Lys Asp Thr Leu Glu Glu
                110                 115                 120

Leu Asp Glu Ile Ala Asn Lys Arg Glu Val Ala Tyr Tyr Arg Ser
                125                 130                 135
```

```
Val Ile Asn Ser Leu Arg Ser Lys Gly Phe Lys Val Ile Val Asn
            140                 145                 150

Leu Asn His Phe Thr Leu Pro Tyr Trp Leu His Asp Pro Ile Glu
            155                 160                 165

Ala Arg Glu Arg Ala Leu Thr Asn Lys Arg Asn Gly Trp Val Asn
            170                 175                 180

Pro Arg Thr Val Ile Glu Phe Ala Lys Tyr Ala Ala Tyr Ile Ala
            185                 190                 195

Tyr Lys Phe Gly Asp Ile Val Asp Met Trp Ser Thr Phe Asn Glu
            200                 205                 210

Pro Met Val Val Glu Leu Gly Tyr Leu Ala Pro Tyr Ser Gly
            215                 220                 225

Phe Pro Pro Gly Val Leu Asn Pro Glu Ala Ala Lys Leu Ala Ile
            230                 235                 240

Leu His Met Ile Asn Ala His Ala Leu Ala Tyr Arg Gln Ile Lys
            245                 250                 255

Lys Phe Asp Thr Glu Lys Ala Asp Lys Asp Ser Lys Glu Pro Ala
            260                 265                 270

Glu Val Gly Ile Ile Tyr Asn Asn Ile Gly Val Ala Tyr Pro Lys
            275                 280                 285

Asp Pro Asn Asp Ser Lys Asp Val Lys Ala Ala Glu Asn Asp Asn
            290                 295                 300

Phe Phe His Ser Gly Leu Phe Phe Glu Ala Ile His Lys Gly Lys
            305                 310                 315

Leu Asn Ile Glu Phe Asp Gly Glu Thr Phe Ile Asp Ala Pro Tyr
            320                 325                 330

Leu Lys Gly Asn Asp Trp Ile Gly Val Asn Tyr Tyr Thr Arg Glu
            335                 340                 345

Val Val Thr Tyr Gln Glu Pro Met Phe Pro Ser Ile Pro Leu Ile
            350                 355                 360

Thr Phe Lys Gly Val Gln Gly Tyr Gly Tyr Ala Cys Arg Pro Gly
            365                 370                 375

Thr Leu Ser Lys Asp Asp Arg Pro Val Ser Asp Ile Gly Trp Glu
            380                 385                 390

Leu Tyr Pro Glu Gly Met Tyr Asp Ser Ile Val Glu Ala His Lys
            395                 400                 405

Tyr Gly Val Pro Val Tyr Val Thr Glu Asn Gly Ile Ala Asp Ser
            410                 415                 420

Lys Asp Ile Leu Arg Pro Tyr Tyr Ile Ala Ser His Ile Lys Met
            425                 430                 435

Ile Glu Lys Ala Phe Glu Asp Gly Tyr Glu Val Lys Gly Tyr Phe
            440                 445                 450

His Trp Ala Leu Thr Asp Asn Phe Glu Trp Ala Leu Gly Phe Arg
            455                 460                 465

Met Arg Phe Gly Leu Tyr Glu Val Asn Leu Ile Thr Lys Glu Arg
            470                 475                 480

Ile Pro Arg Glu Lys Ser Val Ser Ile Phe Arg Glu Ile Val Ala
            485                 490                 495

Asn Asn Gly Val Thr Lys Lys Ile Glu Glu Glu Leu Leu Arg Gly
            500                 505                 510
```

(2) INFORMATION FOR SEQ ID NO:2:

(i) SEQUENCE CHARACTERISTICS:
        (A) LENGTH: 1533 base pairs (B) TYPE: nucleic acid
        (C) STRANDEDNESS: double
        (D) TOPOLOGY: linear (ii) MOLECULE TYPE: genomic DNA (iii) HYPOTHETICAL: NO (iv) ANTI-SENSE: NO (vi) ORIGINAL SOURCE:
        (A) ORGANISM: Pyrococcus furiosus (xi) SEQUENCE DESCRIPTION: SEQ ID NO:2:

```
ATGTTCCCTG AAAAGTTCCT TTGGGGTGTG GCACAATCGG GTTTTCAGTT TGAAATGGGG      60

GATAAACTCA GGAGGAATAT TGACACTAAC ACTGATTGGT GGCACTGGGT AAGGGATAAG     120

ACAAATATAG AGAAAGGCCT CGTTAGTGGA GATCTTCCCG AGGAGGGGAT TAACAATTAC     180

GAGCTTTATG AGAAGGACCA TGAGATTGCA AGAAAGCTGG GTCTTAATGC TTACAGAATA     240

GGCATAGAGT GGAGCAGAAT ATTCCCATGG CCAACGACAT TTATTGATGT TGATTATAGC     300

TATAATGAAT CATATAACCT TATAGAAGAT GTAAAGATCA CCAAGGACAC TTTGGAGGAG     360

TTAGATGAGA TCGCCAACAA GAGGGAGGTG GCCTACTATA GGTCAGTCAT AAACAGCCTG     420

AGGAGCAAGG GGTTTAAGGT TATAGTTAAT CTAAATCACT TCACCCTTCC ATATTGGTTG     480

CATGATCCCA TTGAGGCTAG GGAGAGGGCG TTAACTAATA AGAGGAACGG CTGGGTTAAC     540

CCAAGAACAG TTATAGAGTT TGCAAAGTAT GCCGCTTACA TAGCCTATAA GTTTGGAGAT     600

ATAGTGGATA TGTGGAGCAC GTTTAATGAG CCTATGGTGG TTGTTGAGCT TGGCTACCTA     660

GCCCCCTACT CTGGCTTCCC TCCAGGGGTT CTAAATCCAG AGGCCGCAAA GCTGGCGATA     720

CTTCACATGA TAAATGCACA TGCTTTAGCT TATAGGCAGA TAAAGAAGTT TGACACTGAG     780

AAAGCTGATA AGGATTCTAA AGAGCCTGCA GAAGTTGGTA TAATTTACAA CAACATTGGA     840

GTTGCTTATC CCAAGGATCC GAACGATTCC AAGGATGTTA AGGCAGCAGA AAACGACAAC     900

TTCTTCCACT CAGGGCTGTT CTTCGAGGCC ATACACAAAG GAAAACTTAA TATAGAGTTT     960

GACGGTGAAA CGTTTATAGA TGCCCCCTAT CTAAAGGGCA ATGACTGGAT AGGGGTTAAT    1020

TACTACACAA GGGAAGTAGT TACGTATCAG GAACCAATGT TTCCTTCAAT CCCGCTGATC    1080

ACCTTTAAGG GAGTTCAAGG ATATGGCTAT GCCTGCAGAC CTGGAACTCT GTCAAAGGAT    1140

GACAGACCCG TCAGCGACAT AGGATGGGAA CTCTATCCAG AGGGGATGTA CGATTCAATA    1200

GTTGAAGCTC ACAAGTACGG CGTTCCAGTT TACGTGACGG AGAACGGAAT AGCGGATTCA    1260

AAGGACATCC TAAGACCTTA CTACATAGCG AGCCACATAA AGATGATAGA GAAGGCCTTT    1320

GAGGATGGGT ATGAAGTTAA GGGCTACTTC CACTGGGCAT TAACTGACAA CTTCGAGTGG    1380

GCTCTCGGGT TTAGAATGCG CTTTGGCCTC TACGAAGTCA ACCTAATTAC AAAGGAGAGA    1440

ATTCCCAGGG AGAAGAGCGT GTCGATATTC AGAGAGATAG TAGCCAATAA TGGTGTTACG    1500

AAAAAGATTG AAGAGGAATT GCTGAGGGGA TGA                                1533
```

(2) INFORMATION FOR SEQ ID NO:3:

(i) SEQUENCE CHARACTERISTICS:
        (A) LENGTH: 491 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Lys Phe Pro Lys Asn Phe Met Phe Gly Tyr Ser Trp Ser Gly
 1               5                  10                  15

Phe Gln Phe Glu Met Gly Leu Pro Gly Ser Glu Val Glu Ser Asp
                 20                  25                  30

Trp Trp Val Trp Val His Asp Lys Glu Asn Ile Ala Ser Gly Leu
                 35                  40                  45

Val Ser Gly Asp Leu Pro Glu Asn Gly Pro Ala Tyr Trp His Leu
                 50                  55                  60

Tyr Lys Gln Asp His Asp Ile Ala Glu Lys Leu Gly Met Asp Cys
                 65                  70                  75

Ile Arg Gly Gly Ile Glu Trp Ala Arg Ile Phe Pro Lys Pro Thr
                 80                  85                  90

Phe Asp Val Lys Val Asp Val Glu Lys Asp Glu Glu Gly Asn Ile
                 95                 100                 105

Ile Ser Val Asp Val Pro Glu Ser Thr Ile Lys Glu Leu Glu Lys
                110                 115                 120

Ile Ala Asn Met Glu Ala Leu Glu His Tyr Arg Lys Ile Tyr Ser
                125                 130                 135

Asp Trp Lys Glu Arg Gly Lys Thr Phe Ile Leu Asn Leu Tyr His
                140                 145                 150

Trp Pro Leu Pro Leu Trp Ile His Asp Pro Ile Ala Val Arg Lys
                155                 160                 165

Leu Gly Pro Asp Arg Ala Pro Ala Gly Trp Leu Asp Glu Lys Thr
                170                 175                 180

Val Val Glu Phe Val Lys Phe Ala Ala Phe Val Ala Tyr His Leu
                185                 190                 195

Asp Asp Leu Val Asp Met Trp Ser Thr Met Asn Glu Pro Asn Val
                200                 205                 210

Val Tyr Asn Gln Gly Tyr Ile Asn Leu Arg Ser Gly Phe Pro Pro
                215                 220                 225

Gly Tyr Leu Ser Phe Glu Ala Ala Glu Lys Ala Lys Phe Asn Leu
                230                 235                 240

Ile Gln Ala His Ile Gly Ala Tyr Asp Ala Ile Lys Glu Tyr Ser
                245                 250                 255

Glu Lys Ser Val Gly Val Ile Tyr Ala Phe Ala Trp His Asp Pro
                260                 265                 270

Leu Ala Glu Glu Tyr Lys Asp Glu Val Glu Glu Ile Arg Lys Lys
                275                 280                 285

Asp Tyr Glu Phe Val Thr Ile Leu His Ser Lys Gly Lys Leu Asp
                290                 295                 300

Trp Ile Gly Val Asn Tyr Tyr Ser Arg Leu Val Tyr Gly Ala Lys
                305                 310                 315

Asp Gly His Leu Val Pro Leu Pro Gly Tyr Gly Phe Met Ser Glu
                320                 325                 330

Arg Gly Gly Phe Ala Lys Ser Gly Arg Pro Ala Ser Asp Phe Gly
                335                 340                 345

Trp Glu Met Tyr Pro Glu Gly Leu Glu Asn Leu Leu Lys Tyr Leu
                350                 355                 360

Asn Asn Ala Tyr Glu Leu Pro Met Ile Ile Thr Glu Asn Gly Met
                365                 370                 375

Ala Asp Ala Ala Asp Arg Tyr Arg Pro His Tyr Leu Val Ser His
                380                 385                 390

Leu Lys Ala Val Tyr Asn Ala Met Lys Glu Gly Ala Asp Val Arg
                395                 400                 405
```

```
    Gly Tyr Leu His Trp Ser Leu Thr Asp Asn Tyr Glu Trp Ala Gln
                    410                 415                 420

Gly Phe Arg Met Arg Phe Gly Leu Val Tyr Val Asp Phe Glu Thr
                425                 430                 435

Lys Lys Arg Tyr Leu Arg Pro Ser Ala Leu Val Phe Arg Glu Ile
                440                 445                 450

Ala Thr Gln Lys Glu Ile Pro Glu Glu Leu Ala His Leu Ala Asp
                455                 460                 465

Leu Lys Phe Val Thr Lys Lys Val Ala Ile Ser Phe Phe Leu Cys
                470                 475                 480

Phe Leu Thr His Ile Phe Gly Lys Ile Arg Ser
                485                 490
```

(2) INFORMATION FOR SEQ ID NO:4:

(i) SEQUENCE CHARACTERISTICS:
        (A) LENGTH: 1476 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:4:

```
ATGAAGTTCC CAAAAAACTT CATGTTTGGA TATTCTTGGT CTGGTTTCCA GTTTGAGATG      60

GGACTGCCAG GAAGTGAAGT GGAAAGCGAC TGGTGGGTGT GGGTTCACGA CAAGGAGAAC     120

ATAGCATCAG GTCTAGTAAG TGGAGATCTA CCAGAGAACG GCCCAGCATA TTGGCACCTC     180

TATAAGCAAG ATCATGACAT TGCAGAAAAG CTAGGAATGG ATTGTATTAG AGGTGGCATT     240

GAGTGGGCAA GAATTTTTCC AAAGCCAACA TTTGACGTTA AGTTGATGT GGAAAAGGAT      300

GAAGAAGGCA ACATAATTTC CGTAGACGTT CCAGAGAGTA CAATAAAAGA GCTAGAGAAA     360

ATTGCCAACA TGGAGGCCCT TGAACATTAT CGCAAGATTT ACTCAGACTG AAGGAGAGG     420

GGCAAAACCT TCATATTAAA CCTCTACCAC TGGCCTCTTC CATTATGGAT TCATGACCCA     480

ATTGCAGTAA GGAAACTTGG CCCGGATAGG GCTCCTGCAG GATGGTTAGA TGAGAAGACA     540

GTGGTAGAGT TTGTGAAGTT TGCCGCCTTC GTTGCTTATC ACCTTGATGA CCTCGTTGAC     600

ATGTGGAGCA CAATGAACGA ACCAAACGTA GTCTACAATC AAGGTTACAT TAATCTACGT     660

TCAGGATTTC CACCAGGATA TCTAAGCTTT GAAGCAGCAG AAAAGGCAAA ATTCAACTTA     720

ATTCAGGCTC ACATCGGAGC ATATGATGCC ATAAAAGAGT ATTCAGAAAA ATCCGTGGGA     780

GTGATATACG CCTTTGCTTG GCACGATCCT CTAGCGGAGG AGTATAAGGA TGAAGTAGAG     840

GAAATCAGAA AGAAAGACTA TGAGTTTGTA ACAATTCTAC ACTCAAAAGG AAAGCTAGAC     900

TGGATCGGCG TAAACTACTA CTCCAGGCTG GTATATGGAG CCAAAGATGG ACACCTAGTT     960

CCTTTACCTG GATATGGATT TATGAGTGAG AGAGGAGGAT TTGCAAAGTC AGGAAGACCT    1020

GCTAGTGACT TTGGATGGGA AATGTACCCA GAGGGCCTTG AGAACCTTCT TAAGTATTTA    1080

AACAATGCCT ACGAGCTACC AATGATAATT ACAGAGAACG GTATGGCCGA TGCAGCAGAT    1140

AGATACAGGC CACACTATCT CGTAAGCCAT CTAAAGGCAG TTTACAATGC TATGAAAGAA    1200

GGTGCTGATG TTAGAGGGTA TCTCCACTGG TCTCTAACAG ACAACTACGA ATGGGCCCAA    1260

GGGTTCAGGA TGAGATTTGG ATTGGTTTAC GTGGATTTCG AGACAAAGAA GAGATATTTA    1320

AGGCCAAGCC CCTGGTATT CAGAGAAATA GCCACTCAAA AAGAAATTCC AGAAGAATTA    1380

GCTCACCTCG CAGACCTCAA ATTTGTTACC AAGAAAGTAG CCATTTCATT TTTTCTTTGT    1440
```

TTTTTAACTC ATATTTTTGG GAAAATAAGA TCATAA                                    1476

(2) INFORMATION FOR SEQ ID NO:5:

(i) SEQUENCE CHARACTERISTICS:
        (A) LENGTH: 491 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
    Met Leu Ser Phe Pro Lys Gly Phe Lys Phe Gly Trp Ser Gln Ser
     1               5                  10                  15

Gly Phe Gln Ser Glu Met Gly Thr Pro Gly Ser Glu Asp Pro Asn
                    20                  25                  30

Ser Asp Trp His Val Trp Val His Asp Arg Glu Asn Ile Val Ser
                    35                  40                  45

Gln Val Val Ser Gly Asp Leu Pro Glu Asn Gly Pro Gly Tyr Trp
                    50                  55                  60

Gly Asn Tyr Lys Arg Phe His Asp Glu Ala Glu Lys Ile Gly Leu
                    65                  70                  75

Asn Ala Val Arg Ile Asn Val Glu Trp Ser Arg Ile Phe Pro Arg
                    80                  85                  90

Pro Leu Pro Lys Pro Glu Met Gln Thr Gly Thr Asp Lys Glu Asn
                    95                 100                 105

Ser Pro Val Ile Ser Val Asp Leu Asn Glu Ser Lys Leu Arg Glu
                   110                 115                 120

Met Asp Asn Tyr Ala Asn His Glu Ala Leu Ser His Tyr Arg His
                   125                 130                 135

Ile Leu Glu Asp Leu Arg Asn Arg Gly Phe His Ile Val Leu Asn
                   140                 145                 150

Met Tyr His Trp Thr Leu Pro Ile Trp Leu His Asp Pro Ile Arg
                   155                 160                 165

Val Arg Arg Gly Asp Phe Thr Gly Pro Thr Gly Trp Leu Asn Ser
                   170                 175                 180

Arg Thr Val Tyr Glu Phe Ala Arg Phe Ser Ala Tyr Val Ala Trp
                   185                 190                 195

Lys Leu Asp Asp Leu Ala Ser Glu Tyr Ala Thr Met Asn Glu Pro
                   200                 205                 210

Asn Val Val Trp Gly Ala Gly Tyr Ala Phe Pro Arg Ala Gly Phe
                   215                 220                 225

Pro Pro Asn Tyr Leu Ser Phe Arg Leu Ser Glu Ile Ala Lys Trp
                   230                 235                 240

Asn Ile Ile Gln Ala His Ala Arg Ala Tyr Asp Ala Ile Lys Ser
                   245                 250                 255

Val Ser Lys Lys Ser Val Gly Ile Ile Tyr Ala Asn Thr Ser Tyr
                   260                 265                 270

Tyr Pro Leu Arg Pro Gln Asp Asn Glu Ala Val Glu Ile Ala Glu
                   275                 280                 285

Arg Leu Asn Arg Trp Ser Phe Phe Asp Ser Ile Ile Lys Gly Glu
                   290                 295                 300

Ile Thr Ser Glu Gly Gln Asn Val Arg Glu Asp Leu Arg Asn Arg
                   305                 310                 315

Leu Asp Trp Ile Gly Val Asn Tyr Tyr Thr Arg Thr Val Val Thr
                   320                 325                 330
```

```
Lys Ala Glu Ser Gly Tyr Leu Thr Leu Pro Gly Tyr Gly Asp Arg
            335                 340                 345

Cys Glu Arg Asn Ser Leu Ser Leu Ala Asn Leu Pro Thr Ser Asp
            350                 355                 360

Phe Gly Trp Glu Phe Phe Pro Glu Gly Leu Tyr Asp Val Leu Leu
            365                 370                 375

Lys Tyr Trp Asn Arg Tyr Gly Leu Pro Leu Tyr Val Met Glu Asn
            380                 385                 390

Gly Ile Ala Asp Ala Asp Tyr Gln Arg Pro Tyr Tyr Leu Val
            395                 400                 405

Ser His Ile Tyr Gln Val His Arg Ala Leu Asn Glu Gly Val Asp
            410                 415                 420

Val Arg Gly Tyr Leu His Trp Ser Leu Ala Asp Asn Tyr Glu Trp
            425                 430                 435

Ser Ser Gly Phe Ser Met Arg Phe Gly Leu Leu Lys Val Asp Tyr
            440                 445                 450

Leu Thr Lys Arg Leu Tyr Trp Arg Pro Ser Ala Leu Val Tyr Arg
            455                 460                 465

Glu Ile Thr Arg Ser Asn Gly Ile Pro Glu Glu Leu Glu His Leu
            470                 475                 480

Asn Arg Val Pro Pro Ile Lys Pro Leu Arg His
            485                 490
```

(2) INFORMATION FOR SEQ ID NO:6:

(i) SEQUENCE CHARACTERISTICS:
        (A) LENGTH: 489 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Met Tyr Ser Phe Pro Asn Ser Phe Arg Phe Gly Trp Ser Gln Ala
 1               5                  10                  15

Gly Phe Gln Ser Glu Met Gly Thr Pro Gly Ser Glu Asp Pro Asn
            20                  25                  30

Thr Asp Trp Tyr Lys Trp Val His Asp Pro Glu Asn Met Ala Ala
            35                  40                  45

Gly Leu Val Ser Gly Asp Leu Pro Glu Asn Gly Pro Gly Tyr Trp
            50                  55                  60

Gly Asn Tyr Lys Thr Phe His Asp Asn Ala Gln Lys Met Gly Leu
            65                  70                  75

Lys Ile Ala Arg Leu Asn Val Glu Trp Ser Arg Ile Phe Pro Asn
            80                  85                  90

Pro Leu Pro Arg Pro Gln Asn Phe Asp Glu Ser Lys Gln Asp Val
            95                  100                 105

Thr Glu Val Glu Ile Asn Glu Asn Glu Leu Lys Arg Leu Asp Glu
            110                 115                 120

Tyr Ala Asn Lys Asp Ala Leu Asn His Tyr Arg Glu Ile Phe Lys
            125                 130                 135

Asp Leu Lys Ser Arg Gly Leu Tyr Phe Ile Leu Asn Met Tyr His
            140                 145                 150

Trp Pro Leu Pro Leu Trp Leu His Asp Pro Ile Arg Val Arg Arg
            155                 160                 165
```

```
Gly Asp Phe Thr Gly Pro Ser Gly Trp Leu Ser Thr Arg Thr Val
                170                 175                 180

Tyr Glu Phe Ala Arg Phe Ser Ala Tyr Ile Ala Trp Lys Phe Asp
                185                 190                 195

Asp Leu Val Asp Glu Tyr Ser Thr Met Asn Glu Pro Asn Val Val
                200                 205                 210

Gly Gly Leu Gly Tyr Val Gly Val Lys Ser Gly Phe Pro Pro Gly
                215                 220                 225

Tyr Leu Ser Phe Glu Leu Ser Arg Arg His Met Tyr Asn Ile Ile
                230                 235                 240

Gln Ala His Ala Arg Ala Tyr Asp Gly Ile Lys Ser Val Ser Lys
                245                 250                 255

Lys Pro Val Gly Ile Ile Tyr Ala Asn Ser Ser Phe Gln Pro Leu
                260                 265                 270

Thr Asp Lys Asp Met Glu Ala Val Glu Met Ala Glu Asn Asp Asn
                275                 280                 285

Arg Trp Trp Phe Phe Asp Ala Ile Ile Arg Gly Glu Ile Thr Arg
                290                 295                 300

Gly Asn Glu Lys Ile Val Arg Asp Asp Leu Lys Gly Arg Leu Asp
                305                 310                 315

Trp Ile Gly Val Asn Tyr Tyr Thr Arg Thr Val Val Lys Arg Thr
                320                 325                 330

Glu Lys Gly Tyr Val Ser Leu Gly Gly Tyr Gly His Gly Cys Glu
                335                 340                 345

Arg Asn Ser Val Ser Leu Ala Gly Leu Pro Thr Ser Asp Phe Gly
                350                 355                 360

Trp Glu Phe Phe Pro Glu Gly Leu Tyr Asp Val Leu Thr Lys Tyr
                365                 370                 375

Trp Asn Arg Tyr His Leu Tyr Met Tyr Val Thr Glu Asn Gly Ile
                380                 385                 390

Ala Asp Asp Ala Asp Tyr Gln Arg Pro Tyr Tyr Leu Val Ser His
                395                 400                 405

Val Tyr Gln Val His Arg Ala Ile Asn Ser Gly Ala Asp Val Arg
                410                 415                 420

Gly Tyr Leu His Trp Ser Leu Ala Asp Asn Tyr Glu Trp Ala Ser
                425                 430                 435

Gly Phe Ser Met Arg Phe Gly Leu Leu Lys Val Asp Tyr Asn Thr
                440                 445                 450

Lys Arg Leu Tyr Trp Arg Pro Ser Ala Leu Val Tyr Arg Glu Ile
                455                 460                 465

Ala Thr Asn Gly Ala Ile Thr Asp Glu Ile Glu His Leu Asn Ser
                470                 475                 480

Val Pro Pro Val Lys Pro Leu Arg His
                485
```

(2) INFORMATION FOR SEQ ID NO:7:

(i) SEQUENCE CHARACTERISTICS:
        (A) LENGTH: 12 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Asp Trp Ile Gly Val Asn Tyr Tyr Ser Arg Leu Val (2) INFORMATION FOR SEQ ID NO:8:

(i) SEQUENCE CHARACTERISTICS:
        (A) LENGTH: 13 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Pro Ala Ser Asp Phe Gly Trp Glu Met Tyr Pro Glu Gly
   1          5             10

(2) INFORMATION FOR SEQ ID NO:9:

(i) SEQUENCE CHARACTERISTICS:
        (A) LENGTH: 23 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Gly Tyr Leu His Trp Ser Leu Thr Asp Asn Tyr Glu Trp Ala Gln
   1          5             10           15

Gly Phe Arg Met Arg Phe Gly Leu
             20

(2) INFORMATION FOR SEQ ID NO:10:

(i) SEQUENCE CHARACTERISTICS:
        (A) LENGTH: 7 amino acid residues
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa at position 4 can be Phe or Ser (xi) SEQUENCE DESCRIPTION: SEQ ID NO:10:

Gly Phe Gln Xaa Glu Met Gly
   1          5

(2) INFORMATION FOR SEQ ID NO:11:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa at position 8 can be Glu or Asn (xi) SEQUENCE DESCRIPTION: SEQ ID NO:11:

Val Ser Gly Asp Leu Pro Glu Xaa Gly
   1          5

(2) INFORMATION FOR SEQ ID NO:12:

(i) SEQUENCE CHARACTERISTICS:
        (A) LENGTH: 9 amino acid residues (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa at position 3 can be Ser or Ala;
            Xaa at position 8 can be Trp, Lys, Arg or Asn (xi) SEQUENCE DESCRIPTION: SEQ ID NO:12:

Glu Trp Xaa Arg Ile Phe Pro Xaa Pro
      1               5

(2) INFORMATION FOR SEQ ID NO:13:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa at position 3 can be Tyr, Leu or
            Ile; Xaa at position 5 can be Leu or Ile (xi) SEQUENCE DESCRIPTION: SEQ ID NO:13:

Leu Pro Xaa Trp Xaa His Asp Pro Ile
      1               5

(2) INFORMATION FOR SEQ ID NO:14:

(i) SEQUENCE CHARACTERISTICS:
        (A) LENGTH: 13 amino acid residues
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa at position 2 can be Phe or Met;
            Xaa at position 6 can be Met or Asn; Xaa at position 9
            can be Val, Tyr, Trp or Gly; Xaa at position 10 can be
            Glu, Asn or Gly; Xaa at position 11 can be Leu, Gln or
            Ala (xi) SEQUENCE DESCRIPTION: SEQ ID NO:14:

Thr Xaa Asn Glu Pro Xaa Val Val Xaa Xaa Xaa Gly Tyr
      1               5                  10

(2) INFORMATION FOR SEQ ID NO:15:

(i) SEQUENCE CHARACTERISTICS:
        (A) LENGTH: 12 amino acid residues
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa at position 2 can be Asn or Gln;
            Xaa at position 5 can be Ala or Ile; Xaa at position 6
            can be Leu, Gly or Arg; Xaa at position 9 can be Arg or
            Asp; Xaa at position 10 can be Gln, Ala or Gly (xi) SEQUENCE DESCRIPTION: SEQ ID NO:15:

Ile Xaa Ala His Xaa Xaa Ala Tyr Xaa Xaa Ile Lys
      1               5                  10

(2) INFORMATION FOR SEQ ID NO:16:

(i) SEQUENCE CHARACTERISTICS:
        (A) LENGTH: 12 amino acid residues
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa at position 9 can be Thr or Ser;
            Xaa at position 11 can be Glu, Leu or Thr (xi) SEQUENCE DESCRIPTION: SEQ ID NO:16:

Asp Trp Ile Gly Val Asn Tyr Tyr Xaa Arg Xaa Val
    1              5                  10

(2) INFORMATION FOR SEQ ID NO:17:

(i) SEQUENCE CHARACTERISTICS:
        (A) LENGTH: 13 amino acid residues
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa at position 2 can be Val, Ala or
            Thr; Xaa at position 5 can be Ile or Phe; Xaa at position
            9 can be Leu, Met or Phe; Xaa at position 10 can be Tyr
            or Phe (xi) SEQUENCE DESCRIPTION: SEQ ID NO:17:

Pro Xaa Ser Asp Xaa Gly Trp Glu Xaa Xaa Pro Glu Gly
    1              5                  10

(2) INFORMATION FOR SEQ ID NO:18:

(i) SEQUENCE CHARACTERISTICS:
        (A) LENGTH: 11 amino acid residues
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa at position 2 can be Ile, Arg or
            Tyr; Xaa at position 3 can be Leu, Tyr or Gln; Xaa at
            position 6 can be Tyr or His; Xaa at position 8 can be
            Ile or Leu; Xaa at position 9 can be Ala or Val (xi) SEQUENCE DESCRIPTION: SEQ ID NO:18:

Asp Xaa Xaa Arg Pro Xaa Tyr Xaa Xaa Ser His
    1              5                  10

(2) INFORMATION FOR SEQ ID NO:19:

(i) SEQUENCE CHARACTERISTICS:
        (A) LENGTH: 23 amino acid residues
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa at position 3 can be Phe or Leu;
            Xaa at position 6 can be Ala or Ser; Xaa at position 8
            can be Thr or Ala; Xaa at position 11 can be Phe or Tyr
            ; Xaa at position 14 can be Ala or Ser; Xaa at position 15 can be Leu, Gln or Ser; Xaa at position 18 can be Arg or Ser (xi) SEQUENCE DESCRIPTION: SEQ ID NO:19:

```
Gly Tyr Xaa His Trp Xaa Leu Xaa Asp Asn Xaa Glu Trp Xaa Xaa Gly Phe
 1               5                  10                  15

Xaa Met Arg Phe Gly Leu
         20
```

(2) INFORMATION FOR SEQ ID NO:20:

(i) SEQUENCE CHARACTERISTICS:
        (A) LENGTH: 7 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Gly Phe Gln Phe Glu Met Gly
 1               5
```

(2) INFORMATION FOR SEQ ID NO:21:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Val Ser Gly Asp Leu Pro Glu Glu Gly
 1               5
```

(2) INFORMATION FOR SEQ ID NO:22:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Glu Trp Ser Arg Ile Phe Pro Trp Pro
 1               5
```

(2) INFORMATION FOR SEQ ID NO:23:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Leu Pro Tyr Trp Leu His Asp Pro Ile
 1               5
```

(2) INFORMATION FOR SEQ ID NO:24:

(i) SEQUENCE CHARACTERISTICS:
        (A) LENGTH: 13 amino acid residues

```
            (B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:24:

Thr Phe Asn Glu Pro Met Val Val Glu Leu Gly Tyr
    1               5                   10

(2) INFORMATION FOR SEQ ID NO:25:

(i) SEQUENCE CHARACTERISTICS:
            (A) LENGTH:  12 amino acid residues
            (B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:25:

Ile Asn Ala His Ala Leu Ala Tyr Arg Gln Ile Lys
    1               5                   10

(2) INFORMATION FOR SEQ ID NO:26:

(i) SEQUENCE CHARACTERISTICS:
            (A) LENGTH:  12 amino acid residues
            (B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:26:

Asp Trp Ile Gly Val Asn Tyr Tyr Thr Arg Glu Val
    1               5                   10

(2) INFORMATION FOR SEQ ID NO:27:

(i) SEQUENCE CHARACTERISTICS:
            (A) LENGTH:  13 amino acid residues
            (B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:27:

Pro Val Ser Asp Ile Gly Trp Glu Leu Tyr Pro Glu Gly
    1               5                   10

(2) INFORMATION FOR SEQ ID NO:28:

(i) SEQUENCE CHARACTERISTICS:
            (A) LENGTH:  11 amino acid residues
            (B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:28:

Asp Ile Leu Arg Pro Tyr Tyr Ile Ala Ser His
    1               5                   10

(2) INFORMATION FOR SEQ ID NO:29:

(i) SEQUENCE CHARACTERISTICS:
            (A) LENGTH:  23 amino acid residues
```

(B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:29:

Gly Tyr Phe His Trp Ala Leu Thr Asp Asn Phe Glu Trp Ala Leu Gly Phe
    1               5                  10                  15

Arg Met Arg Phe Gly Leu
                20

(2) INFORMATION FOR SEQ ID NO:30:

(i) SEQUENCE CHARACTERISTICS:
            (A) LENGTH:  9 amino acid residues
            (B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:30:

Glu Trp Ala Arg Ile Phe Pro Lys Pro
    1               5

(2) INFORMATION FOR SEQ ID NO:31:

(i) SEQUENCE CHARACTERISTICS:
            (A) LENGTH:  9 amino acid residues
            (B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:31:

Leu Pro Leu Trp Ile His Asp Pro Ile
    1               5

(2) INFORMATION FOR SEQ ID NO:32:

(i) SEQUENCE CHARACTERISTICS:
            (A) LENGTH:  13 amino acid residues
            (B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:32:

Thr Met Asn Glu Pro Asn Val Val Tyr Asn Gln Gly Tyr
    1               5                  10

(2) INFORMATION FOR SEQ ID NO:33:

(i) SEQUENCE CHARACTERISTICS:
            (A) LENGTH:  12 amino acid residues
            (B) TYPE:  amino acid
            (C) STRANDEDNESS:  single
            (D) TOPOLOGY:  linear (ii) MOLECULE TYPE: peptide (xi) SEQUENCE DESCRIPTION: SEQ ID NO:33:

Ile Gln Ala His Ile Gly Ala Tyr Asp Ala Ile Lys
    1               5                  10

(2) INFORMATION FOR SEQ ID NO:34:

(i) SEQUENCE CHARACTERISTICS:
    (A) LENGTH: 11 amino acid residues
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:34:

Asp Arg Tyr Arg Pro His Tyr Leu Val Ser His
 1               5                   10